(12) United States Patent
Cinbis

(10) Patent No.: US 8,983,620 B2
(45) Date of Patent: Mar. 17, 2015

(54) SYSTEMS, APPARATUS AND METHODS FACILITATING LONGEVITY EXTENSION FOR IMPLANTABLE MEDICAL DEVICES

(71) Applicant: Medtronic, Inc., Minneapolis, MN (US)

(72) Inventor: Can Cinbis, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/836,978

(22) Filed: Mar. 15, 2013

(65) Prior Publication Data

US 2014/0277286 A1 Sep. 18, 2014

(51) Int. Cl.
*A61N 1/37* (2006.01)
*A61N 1/372* (2006.01)

(52) U.S. Cl.
CPC .................................. *A61N 1/37276* (2013.01)
USPC ........................................................... 607/60

(58) Field of Classification Search
None
See application file for complete search history.

(56) References Cited

U.S. PATENT DOCUMENTS

| | | | |
|---|---|---|---|
| 5,423,334 A | 6/1995 | Jordan | |
| 6,115,636 A | 9/2000 | Ryan | |
| 7,831,828 B2 | 11/2010 | Von Arx et al. | |
| 7,932,825 B2 | 4/2011 | Berger | |
| 8,265,556 B2 | 9/2012 | Tekin et al. | |
| 2004/0260363 A1 | 12/2004 | Arx et al. | |
| 2005/0203582 A1 | 9/2005 | Healy et al. | |
| 2006/0025834 A1 | 2/2006 | Von Arx et al. | |
| 2006/0079179 A1 | 4/2006 | Shen | |
| 2006/0116744 A1 | 6/2006 | Von Arx et al. | |
| 2008/0262573 A1* | 10/2008 | Seeberger et al. | 607/60 |
| 2008/0288029 A1 | 11/2008 | Healy et al. | |
| 2008/0294219 A1* | 11/2008 | Osypka et al. | 607/32 |
| 2010/0161003 A1 | 6/2010 | Malmberg et al. | |
| 2010/0198279 A1 | 8/2010 | Corndorf et al. | |
| 2010/0321163 A1 | 12/2010 | Stevenson | |
| 2011/0066211 A1 | 3/2011 | Von Arx et al. | |
| 2011/0160801 A1* | 6/2011 | Markowitz et al. | 607/60 |
| 2011/0190852 A1* | 8/2011 | Dinsmoor et al. | 607/60 |

* cited by examiner

*Primary Examiner* — Paula J Stice
(74) *Attorney, Agent, or Firm* — Michael J. Ostrom; Stephen W. Bauer

(57) ABSTRACT

Systems, apparatus and methods for extension of longevity of implantable medical devices (IMDs) are provided. An apparatus includes a battery, a first communication component configured to provide a first communication type and to be powered by the battery, a second communication component configured to provide a second communication type, and a processor configured to switch on the first communication component or the second communication component to perform communication based, at least, on a defined condition being satisfied. In one embodiment, the first component is a radio frequency (RF) component and the second component is a component that requires less battery power than the RF component. The second component can include a component configured to perform communication based on inductive coupling or based on tissue conductance communication.

11 Claims, 17 Drawing Sheets

SYSTEMS, APPARATUS AND METHODS FACILITATING LONGEVITY EXTENSION FOR IMPLANTABLE MEDICAL DEVICES

TECHNICAL FIELD

The subject disclosure relates generally to implantable medical devices (IMDs) and, more particularly, to systems, apparatus and methods facilitating longevity extension for IMDs.

BACKGROUND

IMDs regularly provide functions for physiological health that are of critical importance in maintaining life as well as quality of life. For example, pacemakers can emit electrical pulses to the heart of the wearer of the IMD upon detection of an abnormal heart rhythm to increase likelihood of the heart beat returning to a normal rate. As another example, an internal defibrillator can emit electrical energy to the heart of the wearer of the IMD upon detection of ventricular fibrillation, cardiac dysrhythmia or pulseless ventricular tachycardia to increase likelihood of the heart returning to a normal sinus rhythm. As another example, an internal neurostimulator can emit electrical energy to the nervous system upon detection of pain signals to increase likelihood of pain interruption. As another example, an internal deep brain stimulation device can emit electrical energy to the brain upon detection of symptoms of neurological movement disorders to increase likelihood of return to greater physiological muscle control.

Medical care providers can monitor the IMD and assess patient current and historical physiological state to predict impending events or conditions. Providers can also initiate and modify treatment plans from time to time and/or evaluate patient compliance with nutrition, exercise and general care regiments based on data recorded in the IMD. Additionally, laboratory personnel can perform IMD diagnostics to improve function efficiencies and detection of low remaining battery life.

While low remaining battery life can be detected, detection can be performed in some instances only when the patient is at a medical facility and the IMD is being monitored. Inaccessibility to device monitoring apparatus is further exacerbated because the expected life span of an IMD (e.g., based on IMD type) can differ from the actual life span due to faults in the IMD, frequency and extent of activity while implanted in the patient and the like. Because IMDs serve life-preserving functions, and surgical intervention is often required to replace IMDs, preserving life span for IMDs is of critical importance and can lead to significant cost savings and/or can improve patient satisfaction with the IMD.

Since typical lithium batteries have an increasing series resistance as the battery is increasingly depleted, during high peak current events, regulated power supplies may go out of regulation due to battery voltage drop. As such, conventional radio frequency (RF) communication-based telemetry schemes may not operate properly as the battery is drained. Further, the longevity labeling for IMDs, which is based on anticipated battery life, can be overly conservative due to margin added to preserve telemetry operation as the battery is depleted. However, overly conservative estimates of longevity can result in waste as some IMDs can continue to function long after the time period indicated via longevity labeling.

SUMMARY

The following presents a simplified summary of one or more of the embodiments in order to provide a basic understanding of various aspects of the embodiments. This summary is not an extensive overview of the embodiments described herein. It is intended to neither identify key or critical elements of the embodiments nor delineate any scope of embodiments or the claims. Its sole purpose is to present some concepts of the embodiments in a simplified form as a prelude to the more detailed description that is presented later. It will also be appreciated that the detailed description may include additional or alternative embodiments beyond those described in the Summary section.

Embodiments described herein include apparatus, methods, and systems facilitating longevity extension of IMDs through the use of alternatives to traditional RF communication. For example, an apparatus can include a battery, a first communication component configured to provide a first communication type and to be powered by the battery, a second communication component configured to provide a second communication type and a processor configured to switch on at least one of the first communication component or the second communication component to perform communication based, at least, on a defined condition being satisfied.

In some embodiments, the first communication component is configured to utilize a first amount of battery power and the second communication component is configured to utilize a second amount of battery power, the second amount being less than the first amount. In this regard, the first communication component can be an RF component and the second communication component can include, but is not limited to, a component configured to perform communication via inductive coupling (e.g., near field communication (NFC)) or a component configured to perform tissue conductance communication. Any number of different types of communication approaches can be employed by the second communication component, and which utilize less battery power than that utilized by a component for RF communication. One or more embodiments herein can switch on the second communication component based on a determination as to whether there is a capability for the battery to provide the power necessary for RF communication. If power is not able to be provided, or the likelihood that power can be provided in the future is less than a defined value, the second communication component can be switched on. As such, switching on particular communication components can facilitate longevity extension.

As another example, even if the battery of an IMD is exhausted, enough power can be provided by an NFC-enabled external device (e.g., interrogation device) for powering an IMD. For example, 1-2 milliamperes (mA) can be generated at an IMD. 1-2 mA can be enough power for operating and interrogating a pacemaker in some embodiments. Selectively switching on a communication component that performs inductive coupling-based communication can facilitate longevity extension.

In another embodiment, a method includes determining, by an IMD system including a processor, a battery, a first communication component and a second communication component, a capability of the battery delivering power required to operate a first type of communication system. The method also includes switching on, by the IMD system, the first communication component or the second communication component based, at least, on whether the required power is able to be delivered. For example, the first type of communication system can be an RF communication system. If the required power for an RF communication system can be delivered to the RF component by the battery, the system switches on the RF component. By contrast, if the required power is not able to be delivered, the system switches on the component associated with a type of communication that uses less power than RF communication. Various different types of communication use less power than RF communication. These communication types include, but are not limited to, inductive coupling communication approaches, tissue conductance communication approaches and the like.

In another embodiment, another method includes: activating a first telemetry session according to a first communication protocol, and receiving a request to close the first telemetry session. The first telemetry session is associated with an IMD. The method also includes determining whether a voltage of a battery associated with the IMD was detected at a value less than a defined threshold during the first telemetry session. The method also includes: transmitting a message to alert a telemetry device that a second telemetry session will be available only via a second communication protocol. The transmitting is performed based, at least, on determining that the voltage was detected at a value less than the defined threshold during the first telemetry session. The method also includes ending the first telemetry session.

In another embodiment, an IMD includes: a battery, a first communication component configured to communicate via a first type of communication, and a second communication component configured to receive power from a device external to a body of a wearer of the IMD. The IMD can also include a power component configured to generate supplemental power for the first communication component based on the power received by the second communication component, wherein the first communication component is configured to be powered by the battery and the supplemental power. In various embodiments different types of power can be received from device including, but not limited to, inductive power.

In another embodiment, an IMD includes a battery, a first communication component configured to transmit a first type of data associated with an IMD via a first type of communication and to be powered by the battery, and a second communication component configured to transmit a second type of data associated with the IMD via a second type of communication. For example, if the first communication component is configured to provide distance telemetry and the second communication component is configured to provide near field telemetry, the first type of data can be non-sensitive data and the second type of data can be sensitive data. As such, the likelihood of interception of sensitive data is reduced since interception can be performed only within the very short range near field.

One or more of the embodiments described herein advantageously facilitate extension of longevity of the IMD through flexibility in IMD assembly configuration allowing the use of different types of communication approaches based on whether the battery of the IMD can deliver enough power to accommodate RF communication.

One or more embodiments also advantageously enable longevity estimates for IMDs to be extended by selectively switching on/off power-intensive communication components based on battery conditions. One or more embodiments can advantageously utilize an inductive coupling-based component for additional power generation for the RF component associated with the IMD. One or more embodiments can advantageously improve security of sensitive data by transmitting sensitive data over the short range facilitated by inductive coupling-based communications while transmitting non-sensitive data via distance telemetry facilitated by typical RF communications.

Toward the accomplishment of the foregoing and related ends, the one or more embodiments can include the aspects hereinafter described and particularly pointed out. The following description, claims and annexed drawings set forth herein detail certain illustrative aspects of one or more of the embodiments. These aspects are indicative, however, of but a few of the various ways in which the principles of various embodiments can be employed, and the described embodiments are intended to include all such aspects and their equivalents.

DETAILED DESCRIPTION

The following detailed description is merely illustrative and is not intended to limit embodiments or application and uses of embodiments. Furthermore, there is no intention to be bound by any expressed or implied theory presented in the preceding Technical Field, Background or Summary sections, or in the following Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the various embodiments. It is evident, however, that the various embodiments can be practiced without these specific details.

Additionally, the following description refers to components being "connected," "coupled," "attached" and/or "adjoined" to one another. As used herein, unless expressly stated otherwise, the terms "connected," "coupled," "attached" and/or "adjoined" mean that one component is directly or indirectly connected to another component, mechanically, electrically or otherwise. Thus, although the figures may depict example arrangements of components, additional and/or intervening components may be present in one or more embodiments.

In addition, the words "example" and "exemplary" are used herein to mean serving as an instance or illustration. Any embodiment or design described herein as "example" or "exemplary" is not necessarily to be construed as preferred or advantageous over other embodiments or designs. Rather, use of the word "example" or "exemplary" is intended to present concepts in a concrete fashion. As used in this application, the term "or" is intended to mean an inclusive "or" rather than an exclusive "or". That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application should generally be construed to mean "one or more" unless specified otherwise or clear from context to be directed to a singular form. The terms "first," "second," "third," and so forth, as used in the claims and description, unless otherwise clear by context, is for clarity only and doesn't necessarily indicate or imply any order in time.

Figure 1:
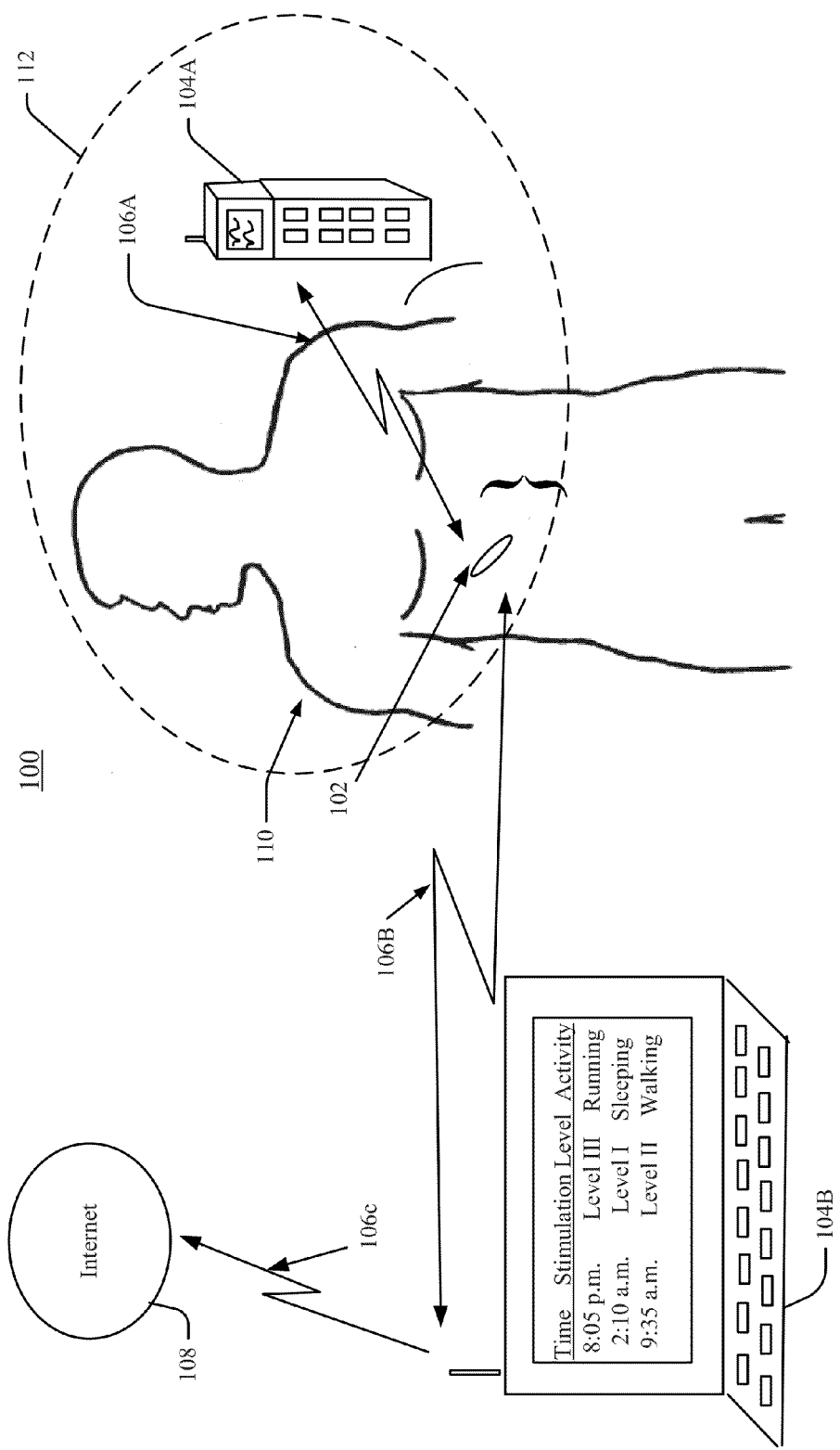
FIG. 1 illustrates a schematic diagram of an exemplary non-limiting medical device telemetry system including an apparatus configured to communicate via various communication methods in accordance with one or more embodiments described herein.

FIG. 1 illustrates a schematic diagram of an exemplary non-limiting medical device system including an apparatus configured to communicate via various communication methods in accordance with one or more embodiments described herein. Medical device telemetry system 100 includes an IMD assembly 102 and one or more external devices 104A, 104B communicatively coupleable to IMD assembly 102 via one or more wireless channels 106A, 106B, 106C. IMD assembly 102 can be implanted within skin, fat and/or muscle of human body 110 and/or injected into the bloodstream of human body 110. IMD 102 and external devices 104A, 104B can be communicatively, inductively, electrically coupled to facilitate one or more operations of medical device telemetry system 100.

IMD assembly 102 can include at least two communication components configured to perform communication according to two different communication protocols. The two different communication protocols can be any number of different wireless communication approaches including, but not limited to, RF communication (e.g., BLUETOOTH®, BLE), inductive coupling communication methods (e.g., NFC) and tissue conductance communication methods. The different communication protocols require different amounts of battery power and, as such, longevity of the IMD can be extended by switching between the two communication components based on, for example, whether the battery in the IMD assembly 102 has capability to provide the required power for the first communication component.

If the battery has the capability to provide the required power, the first communication component can be switched on. As such, subsequent or current telemetry over wireless communication channels 106A, 106B can be performed employing the first communication component (and the corresponding communication protocol of the first communication component). However, if the battery does not have the capability to provide the required power for the first communication component, the second communication component can be switched on. As such, subsequent or current telemetry over wireless communication channels 106A, 106B can be performed employing the second communication component (and the corresponding communication protocol of the second communication component).

In various embodiments, the IMD assembly 102 and external devices 104A, 104B can be configured to perform passive mode or active mode inductive coupling-based communication. For example, in passive mode communication, the IMD assembly 102 can be a target device and external device 104A can read information stored at a chip of the IMD assembly 102. IMD assembly 102 is solely powered by inductive power from external device 104A. In active mode, IMD assembly 102 and external device 104A are each powered by a battery to generate respective magnetic fields. IMD assembly 102 and external device 104A communicate with one another via the established magnetic field.

IMD assembly 102 can include or be an implantable device configured to output an electrical signal to human body 110 and/or monitor fluid, nerves, organ activity and/or other physiological condition of human body 110. In different embodiments, IMD assembly 102 can include, but is not limited to, a pacemaker, an implantable neurostimulator, an implantable cardioverter defibrillator, an implantable physiological monitor and/or an implantable therapy lead.

IMD assembly 102 can be configured to transmit and/or receive information to and/or from external device 104A (and/or external device 104B). By way of example, but not limitation, IMD assembly 102 can transmit information indicative of a biological event of human body 110, current and/or historical data generated by IMD assembly 102, remaining battery life for IMD assembly 102, whether required battery power is available to support RF communication, whether subsequent telemetry sessions will be conducted via RF communication or another type of communication and/or diagnostic information associated with functionality and/or operation of IMD assembly 102. By way of other examples, but not limitation, IMD assembly 102 can receive from external device 104A (and/or external device 104B) information indicative of one or more parameter values by which IMD assembly 102 operates. The information can be received at IMD assembly 102 and/or a processor (not shown) for IMD assembly 102 and cause IMD assembly 102 to modify parameter values by which IMD assembly 102 operates.

In some embodiments, IMD assembly 102 can transmit and/or receive information indicative of past or current activity (e.g., heart rhythms, heart rate, arterial blood oxygen saturation, cardiac output, intravascular pressures, blood pressure, blood temperature, blood oxygen level, heart electrical activity, brain electrical activity, level of quinolinic acid, neurotransmitters, nerve activity, nerve-muscle activity or spinal cord nerve activity). In some embodiments, IMD assembly 102 can transmit and/or receive information indicative of past or current events (e.g., heart attacks, heart failure, arrhythmias, unrecognized myocardial infarctions, chronic pain nerve signals, brain aneurysms, neurological injury, stroke, brain injury). In some embodiments, IMD assembly 102 can transmit and/or receive information to cause IMD assembly 102 to perform any number of functions including, but not limited to, outputting electrical signals to one or more organs, nervous system and/or spinal cord in human body 110, brain stimulation, interruption of pain signals, spinal cord stimulation, monitoring and/or sensing activity of one or more organs in human body 110 and/or monitoring and/or identification of defined chemicals (or levels of defined chemicals) in human body 110.

External devices 104A, 104B can be or include any type of device configured to process, store, display, analyze and/or test medical device telemetry data. For example, external devices 104A, 104B can include, but are not limited to, medical device programmers, remote patient monitoring devices, personal computers, laptops, smart phones or the like. In various embodiments, one or more of external devices 104A, 104B can include programs, modules, hardware, software and/or computer-readable storage media to facilitate monitoring, testing, analyzing, processing, storage and/or display of data associated with information retrieved from one or more of IMD assembly 102. One or more of external devices 104A, 104B can include, or be communicatively coupled to, a receiver (not shown) configured to receive signals from one or more of antennas (not shown) and/or one or more devices (e.g., IMD assembly 102). One or more of external devices 104A, 104B can be communicatively coupled to a transmitter and/or receiver configured to transmit and/or receive information.

One or more of external devices 104A, 104B can transmit information to one or more of IMD assembly 102 to update operation of IMD assembly 102. By way of example, but not limitation, one or more of external devices 104A, 104B can transmit information IMD assembly 102 to cause an update in parameter values to change operation of IMD assembly 102. In particular, the information transmitted from one or more of external devices 104A, 104B can be received at IMD assembly 102 to cause a modification in operation of IMD assembly 102.

Figure 2:
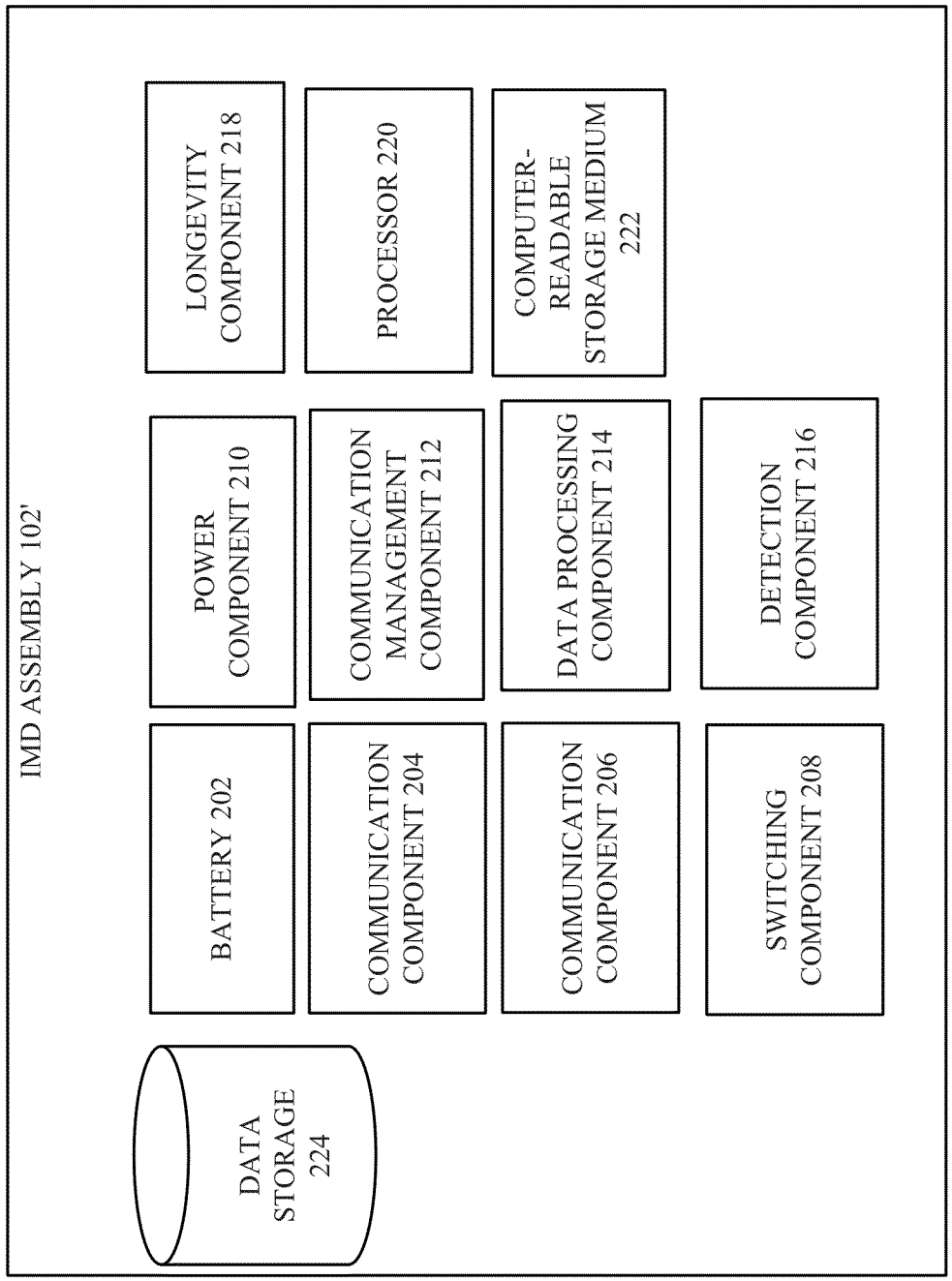
FIG. 2 illustrates a block diagram of an exemplary non-limiting IMD assembly in accordance with one or more embodiments described herein.
Figure 3B:
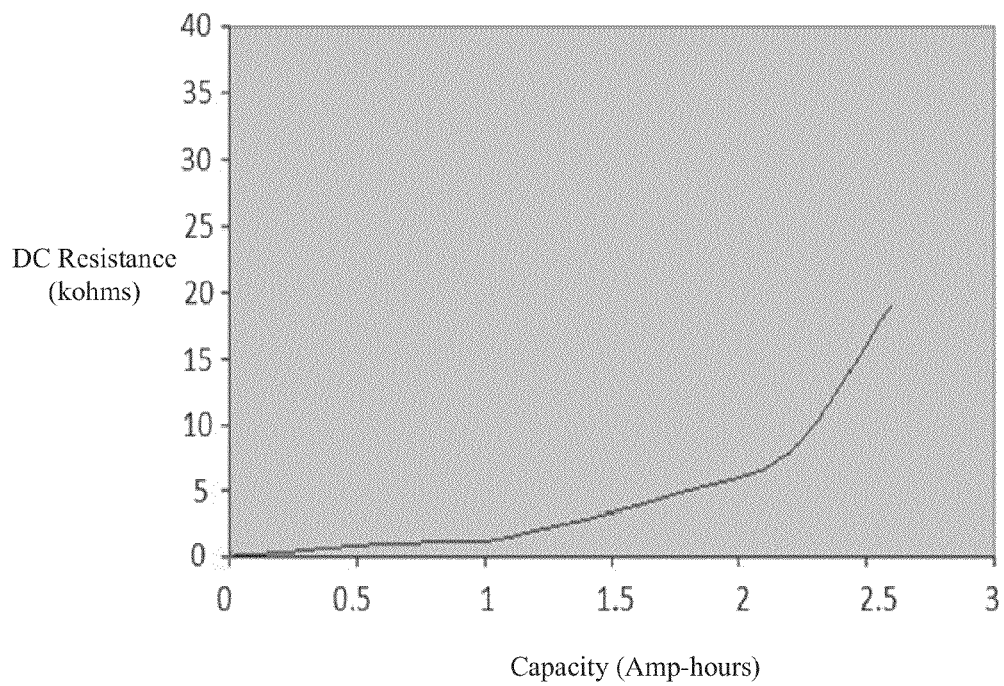
FIGS. 3A and 3B illustrate respective exemplary non-limiting graphs of voltage versus capacity operation, and DC resistance versus capacity operation, for a battery of an IMD assembly in accordance with one or more embodiments described herein.
Figure 3A:
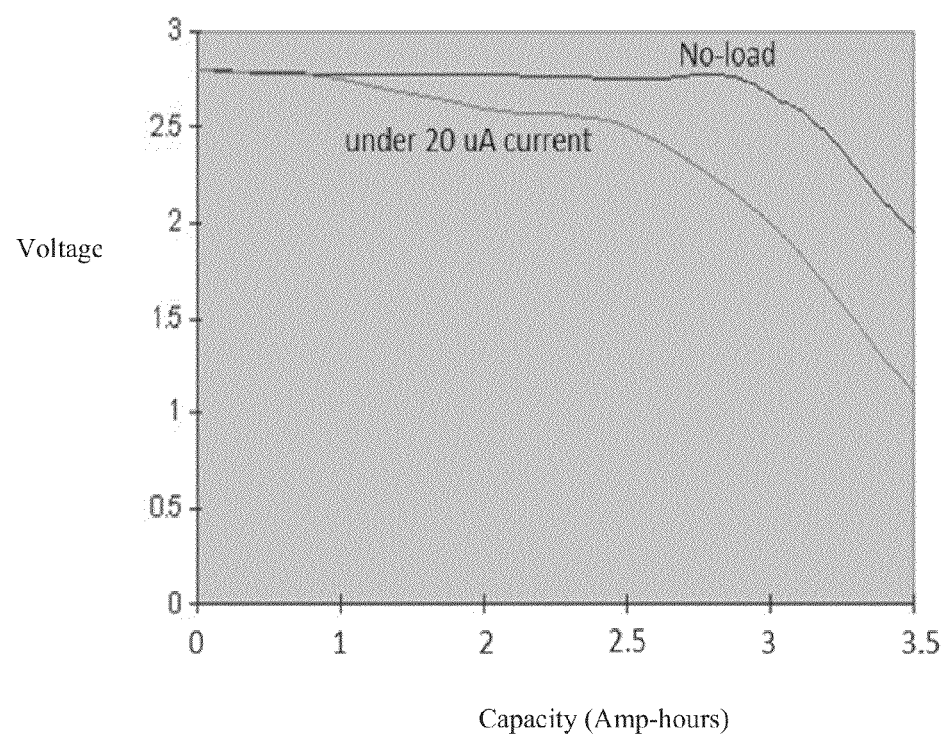
Figure 4:
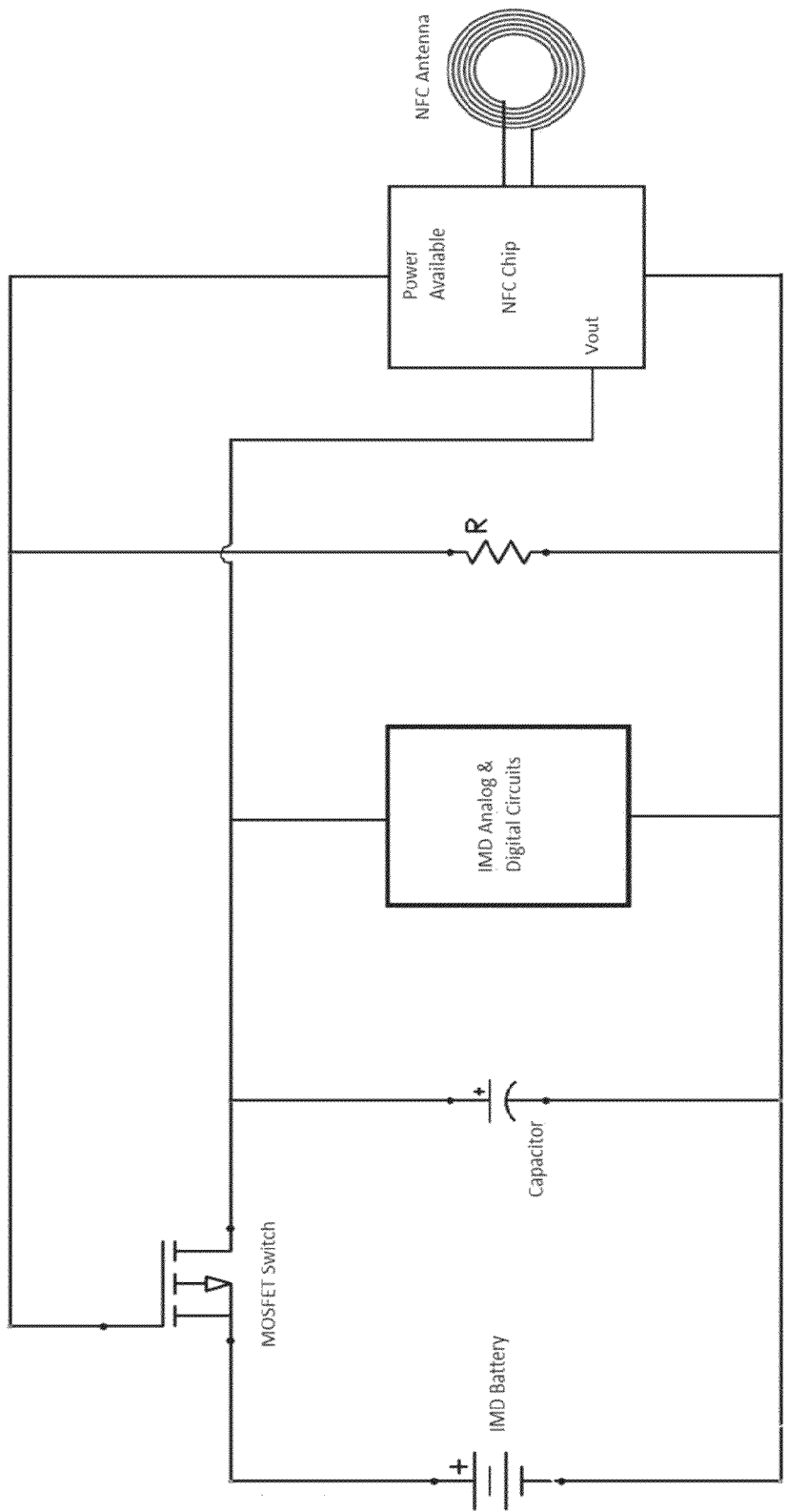
FIG. 4 illustrates an exemplary non-limiting circuit diagram of a power switch for an inductive coupling communication component of an IMD assembly in accordance with one or more embodiments described herein.

More detailed exemplary structure and functionality of an IMD assembly can be as described with reference to FIGS. 2, 3A, 3B and 4. FIG. 2 illustrates a block diagram of an exemplary non-limiting IMD assembly in accordance with one or more embodiments described herein. FIGS. 3A and 3B illustrate respective exemplary non-limiting graphs of voltage versus capacity operation, and DC resistance versus capacity operation, for a battery of an IMD assembly in accordance with one or more embodiments described herein. FIG. 4 illustrates an exemplary non-limiting circuit diagram of a power switch of an IMD assembly in accordance with one or more embodiments described herein.

Turning first to FIG. 2, as shown, IMD assembly 102' includes battery 202, communication component 204, communication component 206, switching component 208, power component 210, communication management component 212, data processing component 214, detection component 216, longevity component 218, processor 220, computer-readable storage medium 222 and/or data storage 224. In various embodiments, one or more of battery 202, communication component 204, communication component 206, switching component 208, power component 210, communication management component 212, data processing component 214, detection component 216, longevity component 218, processor 220, computer-readable storage medium 222 and/or data storage 224 are electrically and/or communicatively coupled to one another to perform one or more functions of IMD assembly 102' described herein.

Battery 202 is configured to provide battery power to communication component 204. In some embodiments, battery 202 is a re-chargeable battery able to be re-charged from inductive power received by communication component 206. In various embodiments, battery 202 is a lithium battery. In other embodiments, any number of different batteries suitable for implantation and configured to provide power to an RF component can be employed.

Communication component 204 and communication component 206 can be configured to provide two different types of communication from IMD assembly 102'. In various embodiments, communication components 204, 206 require different amounts of power from battery 202, based on the different protocols according to which communication components 204, 206 operate. As such, IMD assembly 102' can switch on communication component 206 if IMD assembly 102' determines that battery 202 does not have the capability to provide sufficient battery power to communication component 204, for example. As such, communication from IMD assembly 102' can be reliably provided and longevity of IMD assembly 102' can be extended.

The two different types of communication can be any number of different types of communication, including, but not limited to, RF communication (e.g., proprietary RF communication protocols, Bluetooth®, or the like), inductive coupling-based communication and tissue conductance communication. For example, communication component 204 can be configured to communicate according to a first type of communication protocol (e.g., RF protocol) and communication component 206 can be configured to communicate according to a second type of communication protocol (e.g., inductive coupling protocol).

In various embodiments, one or more components of communication component 204, or the entirety of communication component 204, can be located outside of a housing for IMD assembly 102' and include one or more electrical feedthroughs electrically coupling communication component 204 to one or more other components of IMD assembly 102'. By contrast, in various embodiments, one or more components of communication component 204, or the entirety of communication component 204, can be located inside of a housing for IMD assembly 102'. For example, communication component 204 can include an antenna configured to emit/receive RF signals, and the antenna can be located inside of or outside of the housing of IMD assembly 102'.

RF communication protocols can include any of a variety of RF schemes including, but not limited to, Bluetooth® or Bluetooth® Low Energy (BLE). The specifications for BLE channels call for operation in frequency band from 2.4 to 2.5 Gigahertz (GHz) and a maximum data rate of approximately 200 kilobits per second (kbps). With new modulation schemes, the maximum data rate can increase in the future.

Other RF communication protocols can include, but are not limited to, any of a variety of proprietary RF protocols, such as MEDTRONIC® CONEXUS® wireless telemetry protocol. For example, a number of proprietary medical device communication protocols are developed for wireless communication over the 401-403 MHz band that has been designated for IMDs or over the 403-406 MHz band reserved for medical equipment, can also be employed.

Inductive coupling-based communication protocols can include any number of different communication approaches that rely on a device inductively coupled to communication component 206, for example, for exchange of data. For example, the communication component 206 can be configured to operate according to the NFC protocol, proprietary communication protocols using inductive coupling (such as those used in pacemakers sold by MEDTRONIC®), or other protocols.

For inductive coupling-based communication protocols, IMD assembly 102' can be inductively coupled with an external interrogator/programmer. A programming device can, for example, include a cable attached to the external interrogator and a head of the interrogator can include an antenna. The antenna can generate a magnetic field which, when brought in close proximity to IMD assembly 102', can be detected and recognized by IMD assembly 102' as a request for information. Through the coils inside of communication component 206, for example, near field inductive coupling can be used to allow communication component 206 and the external interrogator to communicate. In these embodiments, communication component 206 is powered by battery 202 and performs active mode near field communication.

In various embodiments, one or more components of communication component 206, or the entirety of communication component 206, can be located outside of a housing for IMD assembly 102' and include one or more electrical feedthroughs electrically coupling communication component 206 to one or more other components of IMD assembly 102'. By contrast, in various embodiments, one or more components of communication component 206, or the entirety of communication component 206, can be located inside of a housing for IMD assembly 102'. For example, communication component 206 can include an antenna that can be located inside of or outside of the housing of IMD assembly 102'.

With regard to NFC protocol, in some embodiments, communication component 206 includes having hardware and/or software configured to perform NFC. In various embodiments, communication component 206 can be configured to perform according to the ISO/IEC 14443 and/or ISO/IEC 18000-3 NFC standards.

Communication component 206 can include a tag having one or more chips (e.g., microchips) and an antenna. The chips are configured to store information received wirelessly at the antenna of the tag from an external device also configured to perform NFC. In various embodiments, the tag can also be configured to perform functions associated with communication, authentication and/or security for communication component 206. In some embodiments, the external device is or includes an interrogating device configured to interrogate the chips of the tag of communication component 206. For example, the antenna of the tag of communication component 206 can receive an interrogation signal. The interrogation signal can be employed for powering communication component 206. The coils in communication component 206 and the coils in the external device create a magnetic field through which information can be exchanged between communication component 206 and the external device.

In some embodiments, communication component 206 operates in a passive mode in which communication component 206 receives inductive power via the antenna of the tag. As such, communication component 206 can be a passive device having no source of power other than the power received from the external device located in the NFC field generated between the two devices. For example, the external device can be placed within 2-5 centimeters from communication component 206 to establish communication.

In other embodiments, however, communication component 206 operates in an active mode in which both communication component 206 and the external device are electrically connected to a power source (e.g., battery) prior to inductive coupling. Both components generate magnetic fields to facilitate transfer of communication. For example, communication component 206 engages with the external device in a back-and-forth communication in which communication component 206 listens/receives data from the external device during a first time period and external device listens/receives data from communication component 206 during a second time period. To avoid collisions, the transmitting device emits the magnetic field while the listening/receiving device switches off the magnetic field during listening/receiving.

Tissue conductance communication protocols, which measure a potential difference between tissue at two points in the body across which a current has been transmitted, can also be employed.

As shown in FIG. 2, IMD assembly 102' can also include switching component 208. Switching component 208 can include hardware and/or software configured to select, switch on/off power to communication component 204 and/or communication component 206.

Switching component 208 switches on the communication component 204 and/or the communication component 206 based on a number of different scenarios as determined by IMD assembly 102'. For example, switching component 208 can be configured to switch on communication component 204 if the IMD assembly 102' determines that sufficient battery power for powering communication component 204 exists, and to switch on communication component 206 if the IMD assembly 102' determines that sufficient battery power for powering communication component 204 does not exist.

Such embodiments can be provided if communication component 204 is configured to utilize a communication protocol that requires greater power from battery 202 than the power required for the communication protocol utilized by communication component 206. By way of example, but not limitation, these embodiments include those for which communication component 204 is configured to provide RF-based communication and communication component 206 is configured to provide inductive coupling-based (active or passive mode) or tissue conductance communication. These embodiments also include those for which two RF-based communication protocols are provided by communication components 204, 206, respectively, but one communication protocol uses more battery power than the other protocol. As an example, communication component 204 can provide communication according to the BLUETOOTH® communication protocol (or the MEDTRONIC® CONEXUS® communication protocol) while communication component 206 can provide communication according to the BLE communication protocol. As another example, communication component 204 can provide communication according to the BLE protocol while communication component 206 can provide communication according to the NFC protocol (or another inductive coupling-based or tissue conductance communication protocol).

In another embodiment, switching component 208 can be configured to switch on communication component 204 if the voltage of battery 202 was not detected at a value less than a defined threshold during a current and/or past telemetry session employing RF communication from communication component 204. The switching component 208 can be configured to switch on communication component 206 if the voltage of battery 202 was detected at a value less than a defined threshold during a current and/or past telemetry session employing RF communication from communication component 204.

FIGS. 3A and 3B illustrate respective exemplary non-limiting graphs of voltage versus capacity operation, and DC resistance versus capacity operation, for a battery of an IMD assembly in accordance with one or more embodiments described herein. FIG. 3A illustrates no-load battery voltage and battery voltage under 20 µA average current drain. Assuming a minimum acceptable loaded battery voltage of 2.2 volts (V) and RF telemetry current of 300 µA, there is approximately 1 amp-hour capacity to use before the battery voltage falls below 2.2 V. However, if end-of-life is declared due to reaching threshold low-battery voltage during telemetry (i.e., assuming communication component 204 is configured to perform RF communication), another 1.5 amp-hour capacity remains that could have been used to support all the other remaining pacemaker operations except RF communication. As such, switching component 208 switching to a communication component that utilizes less power (e.g., NFC protocols) can extend the longevity of the IMD assembly.

FIG. 4 illustrates an exemplary non-limiting circuit diagram of a power switch of an IMD assembly in accordance with one or more embodiments described herein. The power switch of FIG. 4 can be included in or communicatively coupled to switching component 208 in various embodiments to switch on communication component 204 or communication component 206. In this embodiment, communication component 206 is configured to perform NFC. Communication component 204 is configured to perform a communication protocol that requires greater battery power than that required by communication component 206.

In the embodiment shown, the coil shown will detect a magnetic field generated by an external coil located outside of the switching component 208. When inductive power is detected at the coil, energy is received inside of the NFC chip. Typically, if no external device has generated a magnetic field that is in close proximity to the coil of FIG. 4, a high impedance state results at the $V_{OUT}$ and Power Available pins. Because the metal oxide semiconductor field effect transistor (MOSFET) is a positive channel metal oxide semiconductor (PMOS) switch, the source of the switch is switched on and the battery (e.g., battery 202) is connected, providing battery power.

However, when a magnetic field is in close proximity to the coil, the PMOS switch turns off and disconnects the battery from the IMD assembly (e.g., IMD assembly 102'). As such, the entirety of the power must be provided by the inductive power generated from the external device therefore preserving battery energy. The capacitor can provide power temporarily during switching from one communication component to another communication component.

As such, switching component 208 can switch on battery power to communication component 204 to perform RF communication and switch off battery power to communication component 204 when inductive power is received at IMD assembly 102'. In some embodiments, however, switching component 208 can selectively switch on/off communication components 204, 206 based on whether the battery power available to communication component 204 (configured to perform RF communication) is sufficient for such power-intensive functions.

Turning back to FIG. 2, as another example, switching component 208 switches on communication component 204 if battery 202 has critically low battery power and/or peak current demand. In some embodiments, during time periods of peak current demand, IMD assembly 102' can monitor current drawn from battery 202 and configure communication component 204 to operate in a duty cycled operational mode. As such, the duty cycled operational mode can be employed to reduce peak current and average current demand on battery 202. Further, reduction in average power consumption by battery 202 when battery 202 is nearing end-of-life can result.

As another example, in some embodiments, switching component 208 switches on communication component 206 for transfer of sensitive patient information (e.g., patient medical history or treatment data) and switches on communication component 204 for transfer of non-sensitive information (e.g., information related to remaining life of battery 202). Such embodiments can be provided if communication component 206 is configured to provide distance telemetry while communication component 204 is configured to provide inductive coupling-based telemetry.

As another example, in some embodiments, switching component 208 switches on communication component 206 for power retrieval functions only and switches on communication component 204 for communication functions (when communication component 206 is configured to retrieve power via inductive coupling). In this embodiment, communication component 206 and communication component 204 can be switched on concurrently.

As another example, in some embodiments, switching component 208 switches on communication component 206 for both power retrieval and communication functions when an NFC-enabled device is within an NFC field of communication component 206 and communication component 206 is configured to perform NFC communication. For example, when a wearer of IMD assembly 102' is also wearing an NFC-enabled wearable device, switching component 208 can be configured to switch on communication component 206.

Numerous other different functions and/or decisions can be made by switching component 208 to switch on/off communication component 206 and/or communication component 204 for extension of longevity of IMD assembly 102'. In some embodiments, artificial intelligence (AI) and statistical approaches can be employed by switching component 208.

Power component 210 can be configured to whether available power in battery 202 is sufficient for power requirements of communication component 204 (i.e., in embodiments in which communication component 204 is configured to perform RF communication).

In some embodiments, when communication component 206 is configured to perform NFC or other inductive coupling-based communication, power component 210 is configured to provide supplemental power retrieved by communication component 206 to battery 202 for re-charging battery 202 and/or to communication component 204 as an additional source of direct power to communication component 204.

Communication management component (CMC) 212 can be configured to transmit one or more signals to cause communication component 206 and/or communication component 204 to operate in one or more different modes and/or to transmit and/or receive certain types of information. For example, in some embodiments, the CMC 212 is configured to output a signal to cause the communication component 206 to perform only power retrieval functions (e.g., inductive coupling power retrieval) in lieu of power retrieval and communication functions. In other embodiments, CMC 212 is configured to output a signal to cause communication component 206 to perform power retrieval and communication functions.

As another example, CMC 212 can be configured to output a signal to data processing component 214 to cause data processing component 214 to select sensitive data for transmission by communication component 206 (e.g., in embodiments in which communication component 206 is configured to perform inductive coupling-based communication). As another example, CMC 212 can be configured to output a signal to data processing component 214 to cause data processing component 214 to select non-sensitive data for transmission by communication component 204 (e.g., in embodiments in which communication component 204 is configured to perform distance telemetry including, but not limited to, RF-based communication).

As another example, CMC 212 can be configured to output a signal to data processing component 214 to cause data processing component 214 to select all patient data of a certain type for a large-scale data dump (for example, upon detection of particular time of day or level of activity by detection component 216).

Data processing component 214 can be configured to categorize, select, sort and/or retrieve data stored at the IMD. For example, in embodiments in which communication component 206 is switched on for transmission of sensitive data associated with patient medical history, data processing component 214 can select patient medical history information for transmission by communication component 206. In embodiments in which communication component 204 is switched on for transmission of non-sensitive data such as IMD remaining battery life, data processing component 214 can select battery life information for transmission by communication component 204.

Detection component 216 can be configured to detect presence of an NFC signal and/or an RF signal in some embodiments. In some embodiments, detection component 216 is configured to detect time of day and/or level of activity of a wearer of the IMD. For example, detection component 216 can include a clock configured to maintain track of time. As another example, detection component 216 can include a motion detector (e.g., gyroscope or accelerometer) configured to determine the amount of motion of a wearer of the IMD assembly 102'. The amount of motion can enable detection component 216 to determine a level of activity of the wearer of IMD assembly 102'. For example, if motion detected is below a first threshold, detection component 216 can determine that the wearer of IMD assembly 102' is resting or sleeping. By contrast, if motion detected is above a second threshold, detection component 216 can determine that the wearer of IMD assembly 102' is running or engaged in a high level of activity.

Longevity component 218 can be configured to store qualitative and/or quantitative information associated with the longevity for an IMD. For example, longevity information can include a number of years that an IMD is estimated to have battery life of a defined level or percentage value, and be free of malfunction. Longevity component 218 can also be configured to store information associated with the time remaining before end-of-life of the IMD, as dictated by the initial longevity estimated for the IMD upon implantation.

Computer-readable storage medium 222 can store computer-executable instructions that, in response to execution, cause IMD assembly 102', including processor 220 of IMD assembly 102', to perform various operations. In some embodiments, the operations include selectively switching on communication component 206 and/or communication component 204 to facilitate longevity extension of IMD assembly, performing communication and/or power retrieval, sorting and/or selecting different types of information for transmission, determining a time of day and/or level of activity of a wearer of an IMD assembly and the like. In various embodiments, computer-readable storage medium 222 can be any number of different types of memory that can store computer-executable instructions, components, IMD data and the like.

Data storage 224 can store any suitable number of different types of information associated with or for operation of IMD assembly 102'. In various embodiments, data storage 224 can store a value indicative of an amount of remaining battery life, one or more threshold values, longevity information, patient treatment and/or medical history information, battery information and the like.

Figure 5:
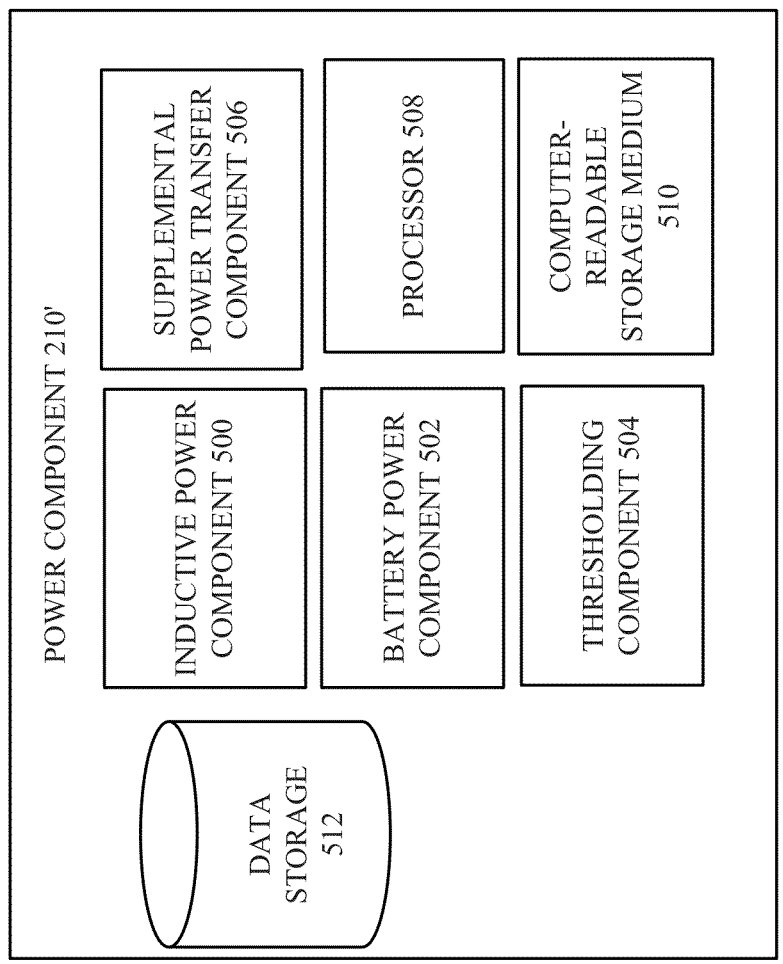
FIG. 5 illustrates a block diagram of an exemplary non-limiting power component for an IMD assembly in accordance with one or more embodiments described herein.

FIG. 5 illustrates an exemplary non-limiting power component for an IMD assembly in accordance with one or more embodiments described herein. As shown, power component 210' can include inductive power component 500, battery power component 502, thresholding component 504, supplemental power transfer component 506, processor 508, computer-readable storage medium 510 and/or data storage 512. In various embodiments, one or more of inductive power component 500, battery power component 502, thresholding component 504, supplemental power transfer component 506, processor 508, computer-readable storage medium 510 and/or data storage 512 can be electrically and/or communicatively coupled to one another to perform one or more functions of power component 210'.

In some embodiments, inductive power component 500 is configured to receive and/or process inductive power received from a device configured to perform inductive coupling-based communication and located external to a body of a wearer of an IMD. Inductive power component 500 can convert inductive power and provide to supplemental power transfer component 506 for use by a communication component of IMD assembly configured to perform RF communication (and which would therefore require battery power). Supplemental power transfer component 506 can be configured to transfer power from the inductive power component 500 to the communication component to provide power to the RF component and/or to the battery to re-charge the battery.

Battery power component 502 can be configured to determine the amount of remaining battery energy in a particular battery (e.g., battery of the IMD assembly), current draw associated with a battery and/or a voltage level associated with a battery during a telemetry session. Thresholding component 504 can be configured to compare the values determined by battery power component 502 to one or more thresholds to determine which communication component should be switched on.

Computer-readable storage medium 510 can be provided. Computer-readable storage medium 510 can store computer-executable instructions that, in response to execution, cause power component 210', including processor 508 of power component 210', to perform various operations. The operations can include comparing the voltage level associated with a battery during a telemetry session to a threshold, for example. Computer-readable storage medium 510 can be any number of different types of memory that can store computer-executable instructions, components, IMD data and the like.

Data storage 512 can store any number of different types of information associated with or for operation of power component 210'. In various embodiments, data storage 512 stores a value of a voltage level associated with a battery during a telemetry session, one or more threshold values or the like.

Figure 6:
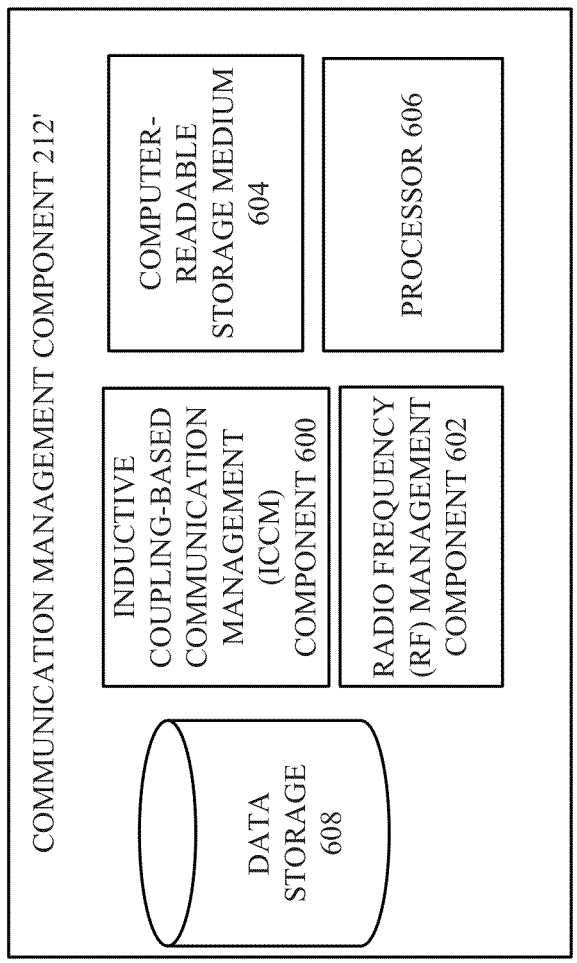
FIG. 6 illustrates an exemplary non-limiting communication management component for an IMD assembly in accordance with one or more embodiments described herein.

FIG. 6 illustrates an exemplary non-limiting CMC for an IMD assembly in accordance with one or more embodiments described herein. CMC 212' includes inductive coupling-based communication management (ICCM) component 600, RF management component 602, computer-readable storage medium 604, processor 606 and/or data storage 608. In one or more embodiments, one or more of ICCM component 600, RF management component 602, computer-readable storage medium 604, processor 606 and/or data storage 608 can be electrically and/or communicatively coupled to one another to perform one or more functions of CMC 212'.

ICCM component 600 determines desired functionality of the inductive coupling-based communication component and causes the component to perform according to such functionality. By way of example, but not limitation, in embodiments in which inductive coupling-based communication is employed for power generation but not for communication, ICCM component 600 can disable the power of the inductive coupling-based communication component utilized for communication and/or otherwise provide a signal including information and/or instructions for not performing communication (and/or for only performing power retrieval).

RF management component 602 determines desired functionality of the RF component and causes the RF component to perform according to such functionality. By way of example, but not limitation, in embodiments in which RF communication is employed for communication of non-sensitive data, ICCM component 600 sends a signal to data processing component 214 causing data processing component 214 to select non-sensitive data for transmission by the RF component.

Computer-readable storage medium 604 can be provided. Computer-readable storage medium 604 can store computer-executable instructions that, in response to execution, cause CMC 412', including processor 606 of CMC 412', to perform various operations. Data storage 608 can store any number of different types of information associated with or for operation of CMC 212'. In various embodiments, computer-readable storage medium 604 can be any number of different types of memory that can store computer-executable instructions, components, IMD data and the like.

Figure 7:
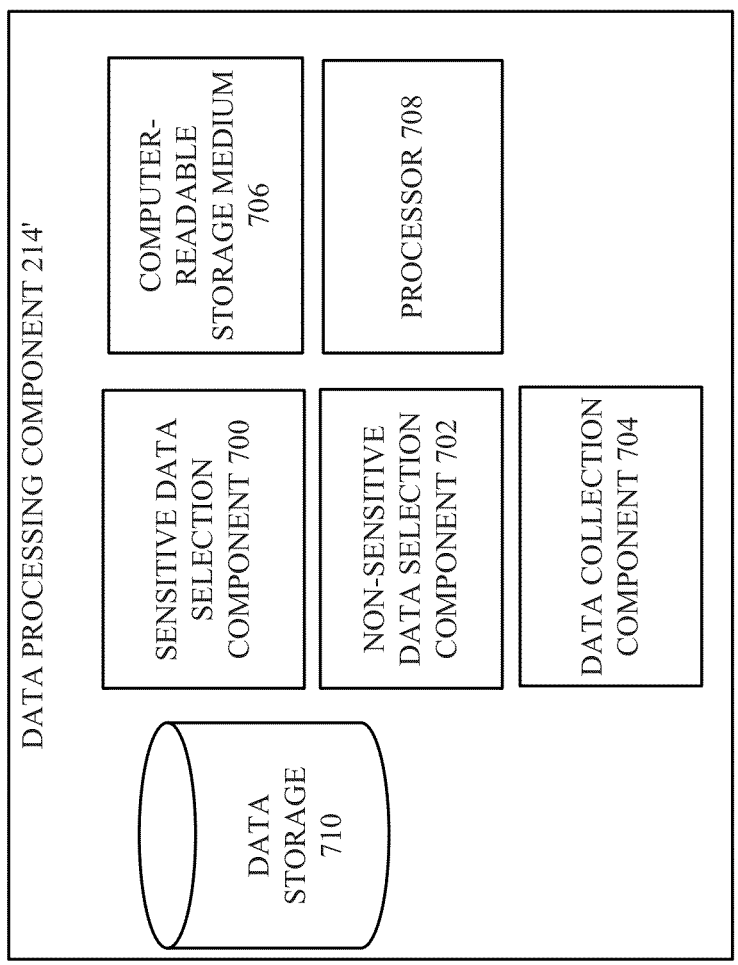
FIG. 7 illustrates an exemplary non-limiting data processing component for an IMD assembly in accordance with one or more embodiments described herein.

FIG. 7 illustrates an exemplary non-limiting data processing component for an IMD assembly in accordance with one or more embodiments described herein. Data processing component 414' includes sensitive data selection component 700, non-sensitive data selection component 702, data collection component 704, computer-readable storage medium 706, processor 708, data storage 710. In various embodiments, one or more of sensitive data selection component 700, non-sensitive data selection component 702, data collection component 704, computer-readable storage medium 706, processor 708, data storage 710 are electrically and/or communicatively coupled to one another to perform one or more functions of data processing component 214'.

Sensitive data selection component 700 and non-sensitive data selection component 702 can be configured to select sensitive data and non-sensitive data, respectively. In some embodiments, sensitive data is current and/or past patient history, treatment information, IMD treatment activity and the like. Non-sensitive data can include, but is not limited to, diagnostic data concerning whether faults have been detected in IMD operation, remaining battery life of the IMD and the like.

Data collection component 704 can be configured to collect large amounts of data in connection with performing data dumps at designated times of day and/or at times corresponding to designated levels of activity of a wearer of the IMD. For example, data collection component 704 can be configured to collect data from an IMD (e.g., pacemaker) for a data dump via NFC communication when a wearer of an IMD is resting/sleeping and/or when the time of day is between 8 p.m. and 4 a.m.

Computer-readable storage medium 706 is provided. Computer-readable storage medium 706 can store computer-executable instructions that, in response to execution, cause data processing component 214', including processor 708 of data processing component 214', to perform various operations. In some embodiments, the operations include selecting sensitive and non-sensitive data, evaluating parameters employed in labeling data as sensitive or non-sensitive. Selecting a certain amount of data for data dumps. Data storage 710 can store any number of different types of information associated with or for operation of data processing component 414'. In various embodiments, computer-readable storage medium 706 can be any number of different types of memory that can store computer-executable instructions, components, IMD data and the like.

Although FIGS. 2 and 5-7 illustrate embodiments that each include a computer-readable storage medium, processor and data storage, in various embodiments, one or more computer-readable storage medium, processor and/or data storage can be employed for more than one of the embodiments. As such, each embodiment need not include separate computer-readable storage media, processors and/or data storage.

Figure 8:
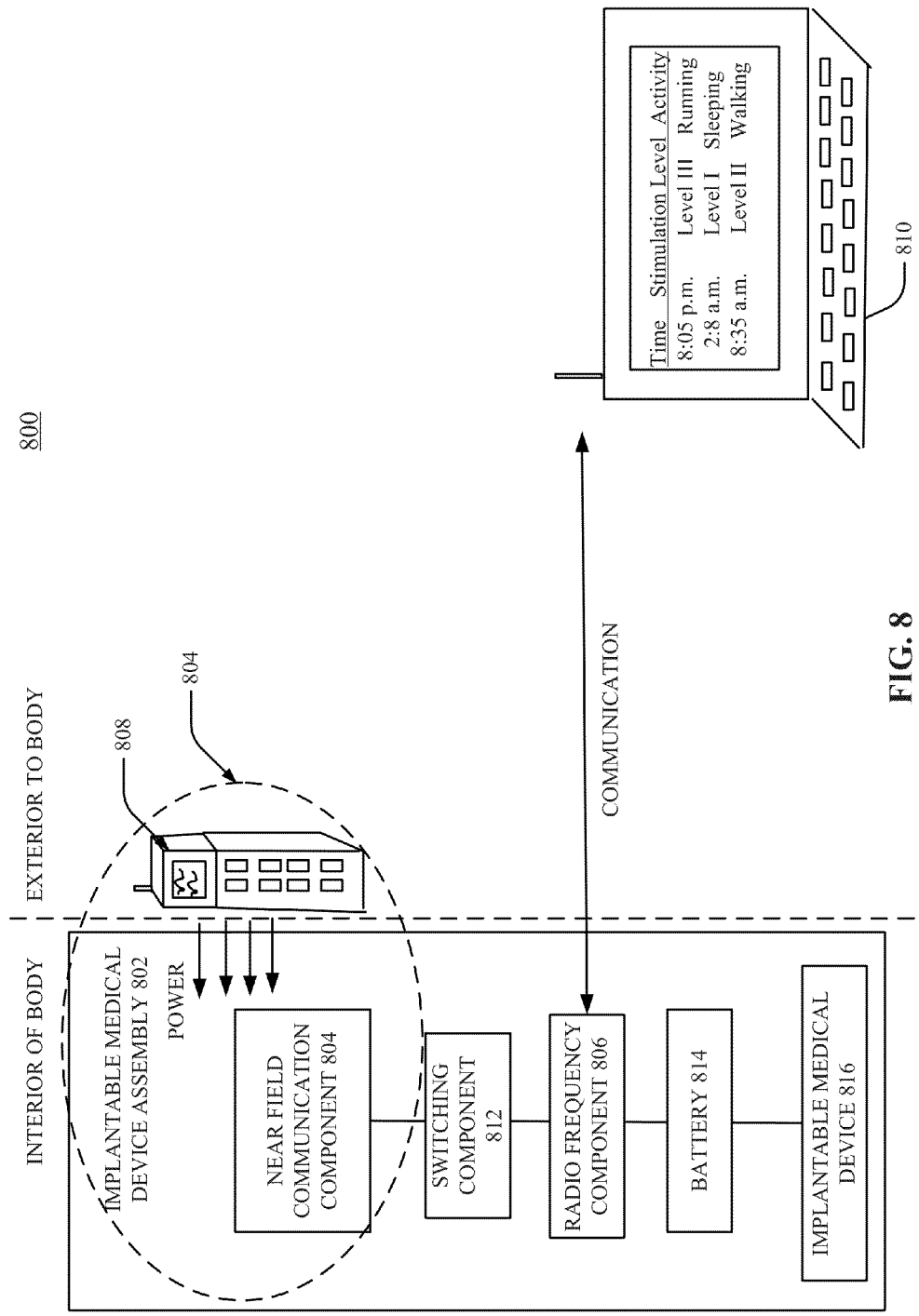
FIG. 8 illustrates a schematic diagram of an exemplary non-limiting medical device telemetry system in which an NFC component performs power acquisition functions via induction and an RF component performs communication functions for the system in accordance with one or more embodiments described herein.

FIG. 8 illustrates a schematic diagram of an exemplary non-limiting medical device telemetry system in which an NFC component performs power acquisition functions via induction and an RF component performs communication functions for the system in accordance with one or more embodiments described herein.

Medical device telemetry system 800 includes IMD assembly 802 and external devices 808, 810. In various embodiments, external device 808 is an NFC-enabled device while external device 810 is configured to conduct RF communication. In various embodiments, components of FIG. 8 can include any of the structure and/or functionality of corresponding components described herein (and vice versa). For example, IMD assembly 802 can include any of the structure and/or functionality of IMD assemblies 102, 902 (and vice versa).

IMD assembly 802 includes NFC component 804, switching component 812, battery 814 and/or RF component 806. In various embodiments, NFC component 804, switching component 812, battery 814 and/or RF component 806 are electrically and/or communicatively coupled to one another to perform one or more of the functions of IMD assembly 802.

As shown, NFC component 804 retrieves power from external device 808 within NFC field 804. RF component 806 conducts RF communication with external device 810. As such, switching component 812 can switch on NFC component 804 and RF component 806 for concurrent yet distinct operation. For example, NFC component 804 can be switched on for power retrieval functions only. RF component 806 can be switched on to perform RF communication functions with external device 810.

In some embodiments, the power retrieved by NFC component 804 can be provided to battery 814 for re-charging the battery thereby extending the life span of IMD 816 in some embodiments.

Figure 9:
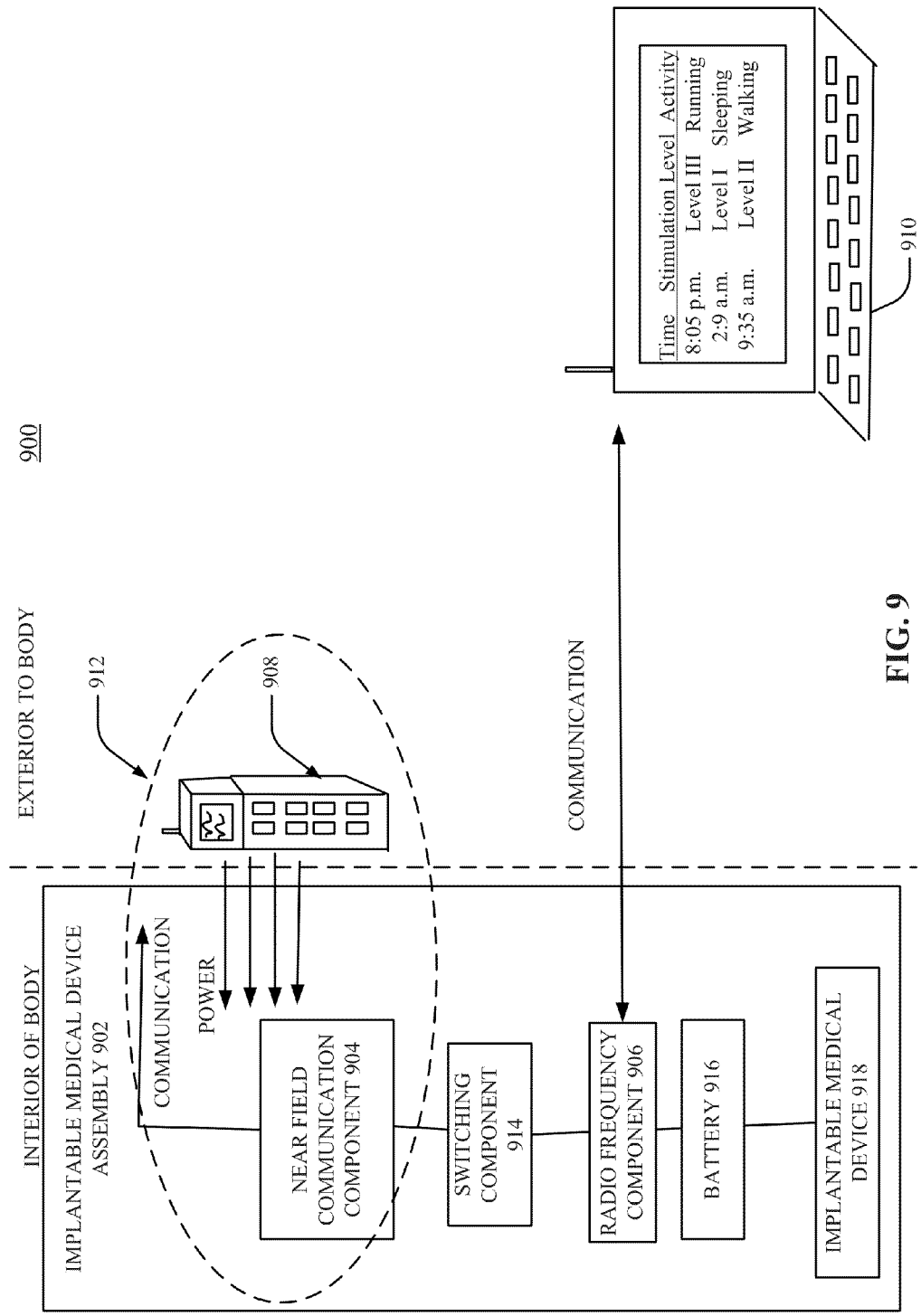
FIG. 9 illustrates a schematic diagram of an exemplary non-limiting medical device telemetry system in which an NFC component performs power acquisition functions via induction and short-range communication functions and an RF component concurrently performs longer-range communication functions for the system in accordance with one or more embodiments described herein.

FIG. 9 illustrates a schematic diagram of an exemplary non-limiting medical device telemetry system in which an NFC component performs power acquisition functions via induction and short-range communication functions and an RF component concurrently performs RF communication functions for the system in accordance with one or more embodiments described herein.

Medical device telemetry system 900 includes IMD assembly 902 and external devices 908, 910. In various embodiments, external device 908 is an NFC-enabled device while external device 910 is configured to conduct RF communication. In various embodiments, components of FIG. 9 can include any of the structure and/or functionality of corresponding components described herein (and vice versa). For example, IMD assembly 902 can include any of the structure and/or functionality of IMD assemblies 102, 802 (and vice versa).

IMD assembly 902 includes NFC component 904, switching component 914, battery 916 and/or RF component 906. In various embodiments, NFC component 904, switching component 914, battery 916 and/or RF component 906 are electrically and/or communicatively coupled to one another to perform one or more of the functions of IMD assembly 902.

As shown, NFC component 904 can conduct NFC communication with external device 908 within NFC field 912. RF component 906 can conduct RF communication with external device 910. Switching component 914 can switch on NFC component 904 and RF component 906 for concurrent yet distinct operation. For example, NFC component 904 can be switched on for power acquisition functions via induction, and short-range communication functions, with external device 908. RF component 906 can be switched on to perform RF communication functions with external device 910.

In some embodiments, the power retrieved by NFC component 904 is provided to battery 916 for re-charging the battery thereby extending the life span of IMD 918 in some embodiments.

In some embodiments, NFC component 904 communicates sensitive data with external device 908. RF component 906 communicates non-sensitive data with external device 910. In various embodiments, sensitive data is current and/or past patient history, treatment information, IMD treatment activity and the like. Non-sensitive data can include, but is not limited to, diagnostic data concerning whether faults have been detected in IMD operation, remaining battery life of the IMD and the like.

In other embodiments, NFC communication is performed by NFC component 904 and RF communication is concurrently performed by RF component 906. For example, NFC is employed over short ranges while information associated with real-time electrograms (EGMs) is transmitted over longer distances.

Figure 10:
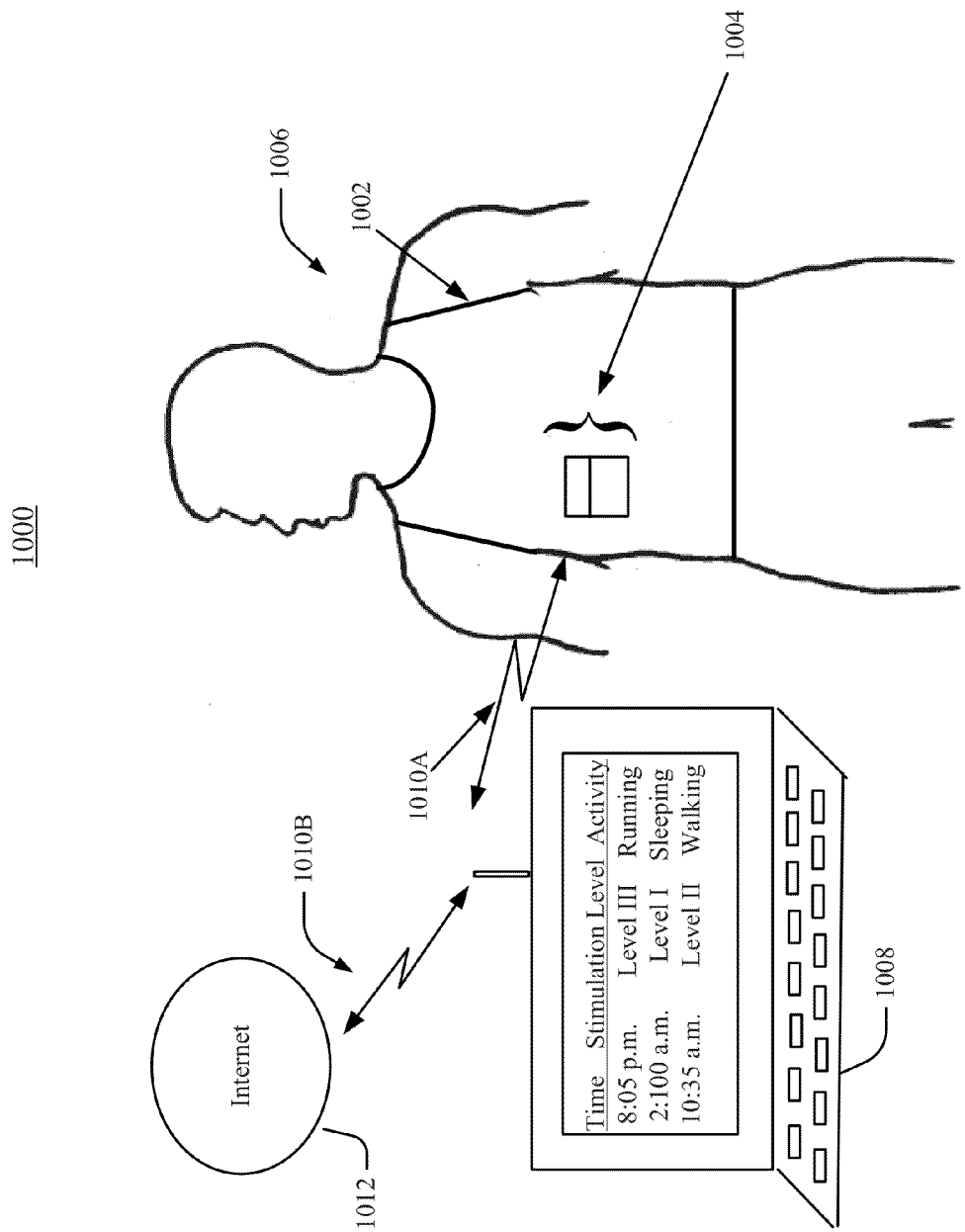
FIG. 10 illustrates a schematic diagram of an exemplary non-limiting medical device telemetry system including a wearable device configured to provide power to an NFC component of the system in accordance with one or more embodiments described herein.

FIG. 10 illustrates a schematic diagram of an exemplary non-limiting medical device telemetry system including a wearable device configured to provide power to an NFC component of the system in accordance with one or more embodiments described herein.

Medical device telemetry system 1000 can include IMD assembly (not shown) and external devices 1002, 1008. In the embodiment shown, external device 1002 is a wearable device configured to provide inductive power and/or perform NFC communication with IMD assembly. In various embodiments, one or more power sources and hardware and/or software for performing NFC communication are provided at NFC component 1004.

While NFC component 1004 is shown disposed in the cardiac region, in other embodiments, any number of other types of wearable devices can be employed and NFC component 1004 can be placed at defined locations within the wearable devices based on the locations at which a patient has an IMD. For example, wearable devices can include baseball caps or hats having NFC components disposed at locations corresponding to locations of IMDs for treatment of brain conditions (e.g., deep brain implants). As another example, wearable devices can include belts having NFC components disposed at locations corresponding to locations at which IMDs are typically implanted for treatment of spinal, nervous conditions and/or organs located in the torso region of the body. In various embodiments, the wearable devices can be tailored for the specific location at which the IMD is implanted as specific location can vary patient-to-patient.

In various embodiments, an RF component (not shown) can provide RF communication with external device 1008 via wireless channels 1010A, 1010B. For example, wireless channel 1010A can be between IMD and external device 1008 and wireless channel 1010B can be between external device 1008 and internet 1012.

FIGS. 11-16 illustrate flow charts of exemplary non-limiting methods of operating IMD assemblies in accordance with embodiments described herein. The methods that follow provide specific examples of communication protocols that can be employed in the methods. The communication methods are merely exemplary and numerous different types of communication methods such as those described in the disclosure can be employed.

Figure 11:
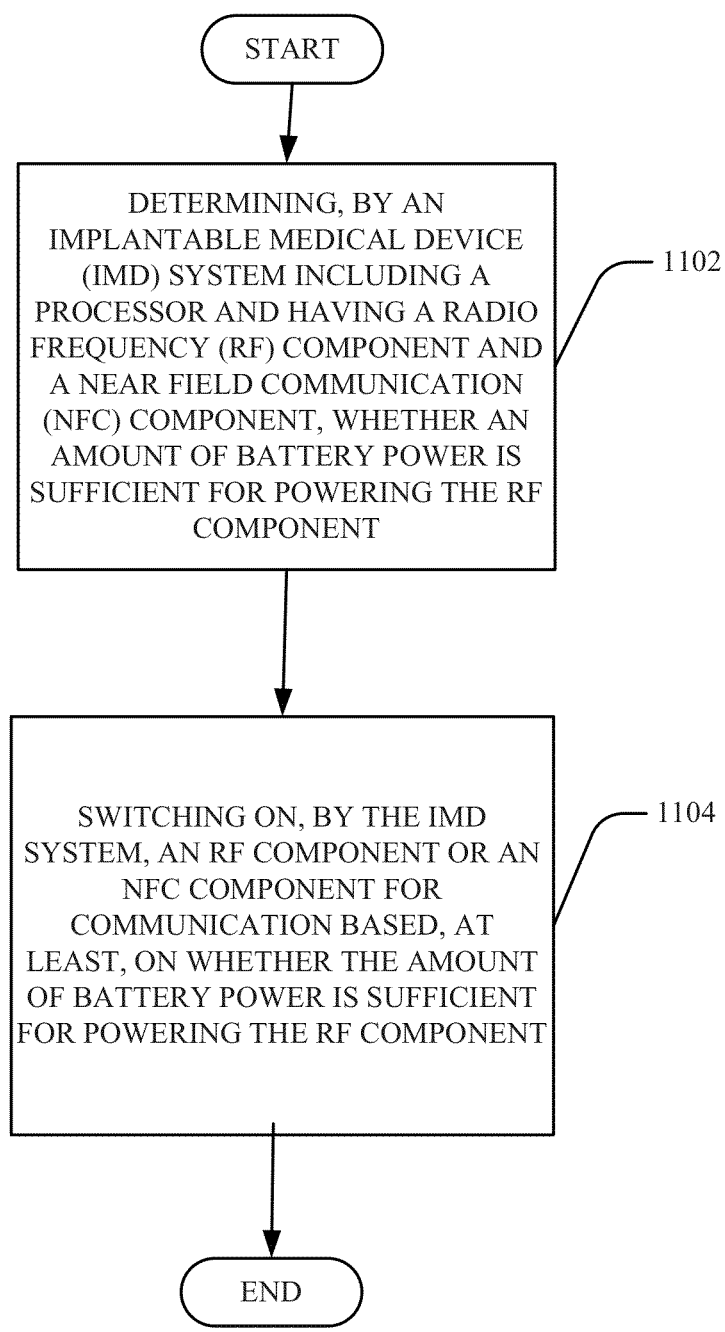
FIGS. 11, 12, 13, 14, 15 and 16 illustrate flow charts of exemplary non-limiting methods of operating IMD assemblies in accordance with embodiments described herein.

Turning first to FIG. 11, at 1102, method 1100 can include determining, by an IMD system including a processor, a battery, a first communication component and a second communication component, a capability of the battery to deliver power required to operate a first type of communication. The first type of communication can be associated with the first communication component.

At 1104, method 1100 can include switching on, by the IMD system, the first communication component or the second communication component based, at least, on the determination made regarding the capability of the battery.

In some embodiments, the first communication component is switched on based on determining that the battery is capable of delivering required power to operate the first type of communication. In some embodiments, the second communication component is switched on based, at least, on determining that the battery is not capable of delivering required power to operate the first type of communication. The first and second types of communication can be any number of different communication types in which the second communication type requires less battery power (or no battery power, such as cases employing passive mode inductive coupling communication). For example, in one embodiment, the first type of communication is RF communication, and the second type of communication is communication based on inductive coupling (e.g., NFC or other inductive coupling approaches) or tissue conductance communication.

Figure 12:
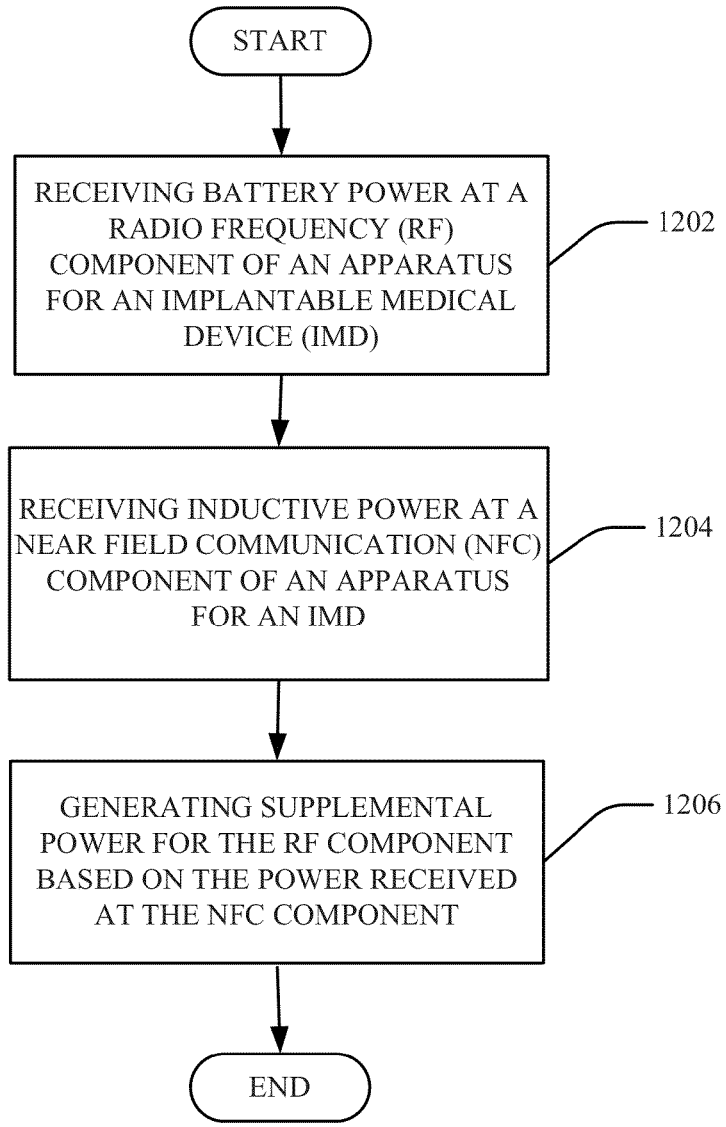

Turning now to FIG. 12, at 1202, method 1200 can include activating a first telemetry session according to a first communication protocol, wherein the telemetry session is associated with IMD. The first telemetry session can be conducted between a patient wearing an IMD and a device external to the body of the patient, for example.

At 1204, method 1200 can include receiving a request to close the first telemetry session. For example, the external device can transmit the request that is received at the IMD after the external device has read and/or transmitted all data that the external device would like to read and/or transmit.

At 1206, method 1200 can include determining whether a voltage of a battery associated with the IMD was detected at a value less than a defined threshold during the first telemetry session. The determination can be made by the IMD prior to closing the first telemetry session, for example. The value can be dependent on the particular implementation of the IMD. For example, different IMDs can have different battery usage patterns and/or sizes. As such, the value that will be a threshold for an IMD will depend on the particular IMD involved in the first telemetry session.

At 1208, method 1200 can include transmitting a message to alert a telemetry device that a second telemetry session will be available only via a second communication protocol. For example, the message can inform the telemetry device that only the communication device that communicates in accordance with the second communication protocol will be switched on should a subsequent telemetry request be detected. Accordingly, if a request is received for communication via the first communication protocol, the request will be rejected.

In some embodiments, transmitting this message is performed based on determining that the voltage was detected at a value less than the defined threshold during the first telemetry session. As such, the IMD system can monitor current and/or past voltage levels during telemetry sessions and determine whether the battery is likely to be able to support a power-intensive communication protocol (e.g., RF communication) in a future telemetry session. If the IMD system determines that support is not likely, the IMD system can send the message that alerts an external device (e.g., medical office equipment) that future sessions must be performed by less power-intensive approaches (e.g., inductive coupling).

In various embodiments, if a determination is made that the voltage of the battery associated with the IMD was not detected at a value less than a defined threshold during the first telemetry session, the IMD need not send a message to the external device and subsequent telemetry sessions can then be provided according to the same communication protocol currently employed during the current telemetry session.

At 1210, method 1200 can include ending the first telemetry session. The first telemetry session can be ended after the message notifying the external system of the type of communication subsequent telemetry sessions should follow.

Figure 13:
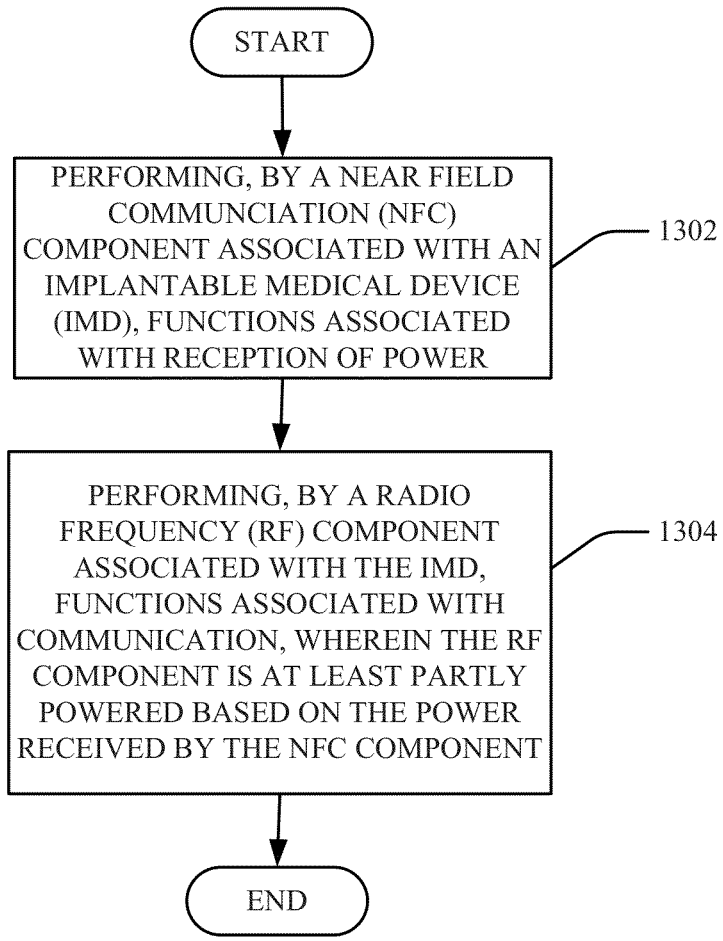

Turning now to FIG. 13, at 1302, method 1300 includes performing, by an NFC component associated with an IMD, functions associated with reception of power. At 1304, method 1300 includes performing, by an RF component associated with the IMD, functions associated with communication for the IMD. In some embodiments, the RF component is partially or solely powered by the power received by the NFC component.

Figure 14:
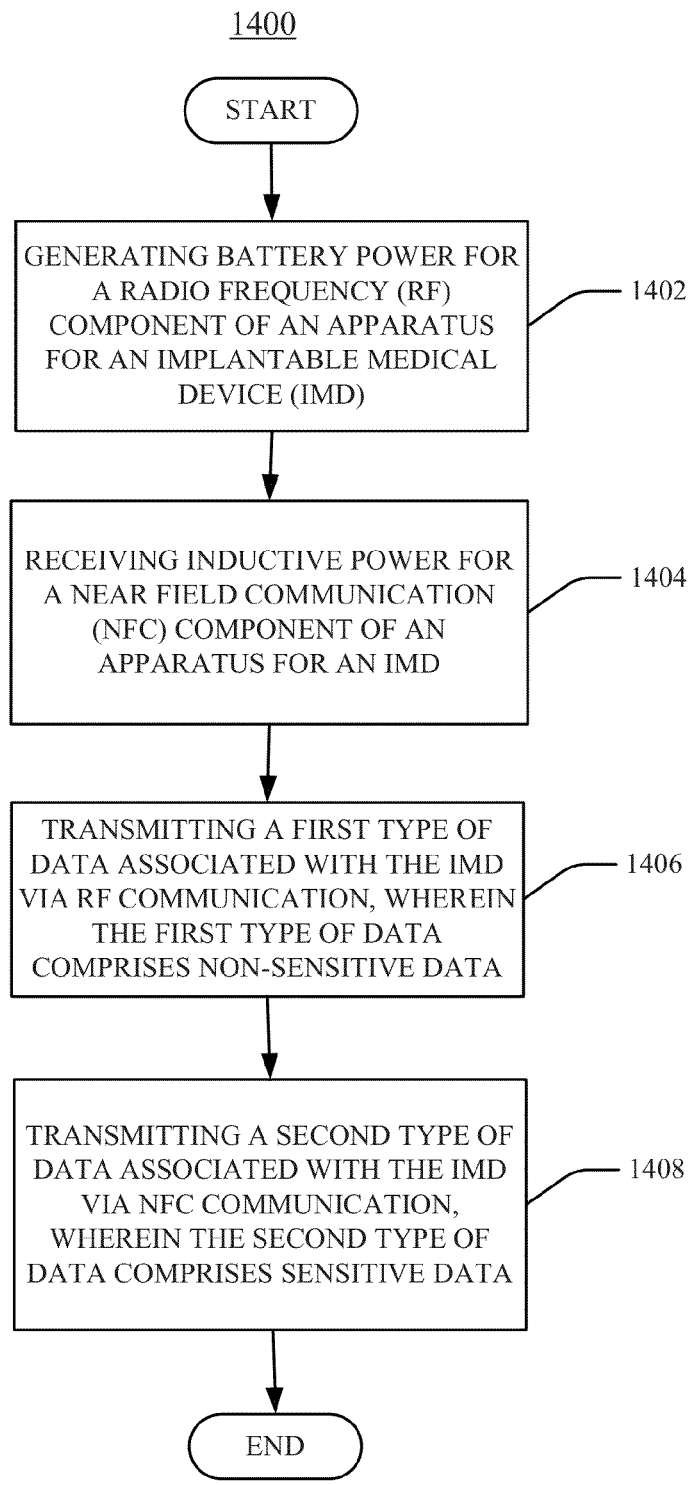

Turning now to FIG. 14, at 1402, method 1400 includes generating power for an RF component of an apparatus for an IMD. At 1404, method 1400 includes receiving inductive power for an NFC component of the apparatus for the IMD.

At 1406, method 1400 includes transmitting a first type of data associated with the IMD via RF communication. The first type of data can be non-sensitive data in various embodiments. Non-sensitive data can include, but is not limited to, diagnostic data concerning whether faults have been detected in IMD operation.

At 1408, method 1400 includes transmitting a second type of data associated with the IMD via NFC communication. The second type of data can be sensitive data. Sensitive data can include, but is not limited to, current and/or historical patient treatment data, current and/or historical information regarding physiological events monitored and/or tracked by the IMD, settings of the IMD associated with treatment.

Accordingly, in various embodiments, the NFC and RF components can concurrently provide communication of different types of data. Secure transmission of sensitive data can be improved by transmitting sensitive data over the short range facilitated by NFC communication while transmitting non-sensitive data over the longer range facilitated by typical RF communications (e.g., BLUE). Because NFC communication is facilitated by placement of an NFC device within 2-5 cm of the body of the wearer of the NFC component (and IMD), the wearer of the IMD is more likely to trust the NFC device (or personnel associated with the NFC device) and provide sensitive data to only trusted parties. Further, because sensitive data can be transmitted only over NFC in this embodiment, the likelihood of data capture by third-party interceptors that may be within a room or other vicinity of the wearer of the NFC component (and IMD) can be reduced as the interception device is not likely to be within 2-5 cm of the body of the wearer of the NFC component (and IMD).

In other embodiments, any number of different types of data can be provided other than sensitive and non-sensitive data. For example, in some embodiments, one of the components (e.g., NFC component or RF component) can provide data at one defined transmission error rate while the other component (e.g., NFC component or RF component) can provide data at another transmission error rate. As an example, numerical data can be considered to be less error-resilient and thus, the component that provides a lower error rate can be employed for numerical data while qualitative data can be provided via the component that has a higher error rate in transmission.

Figure 15:
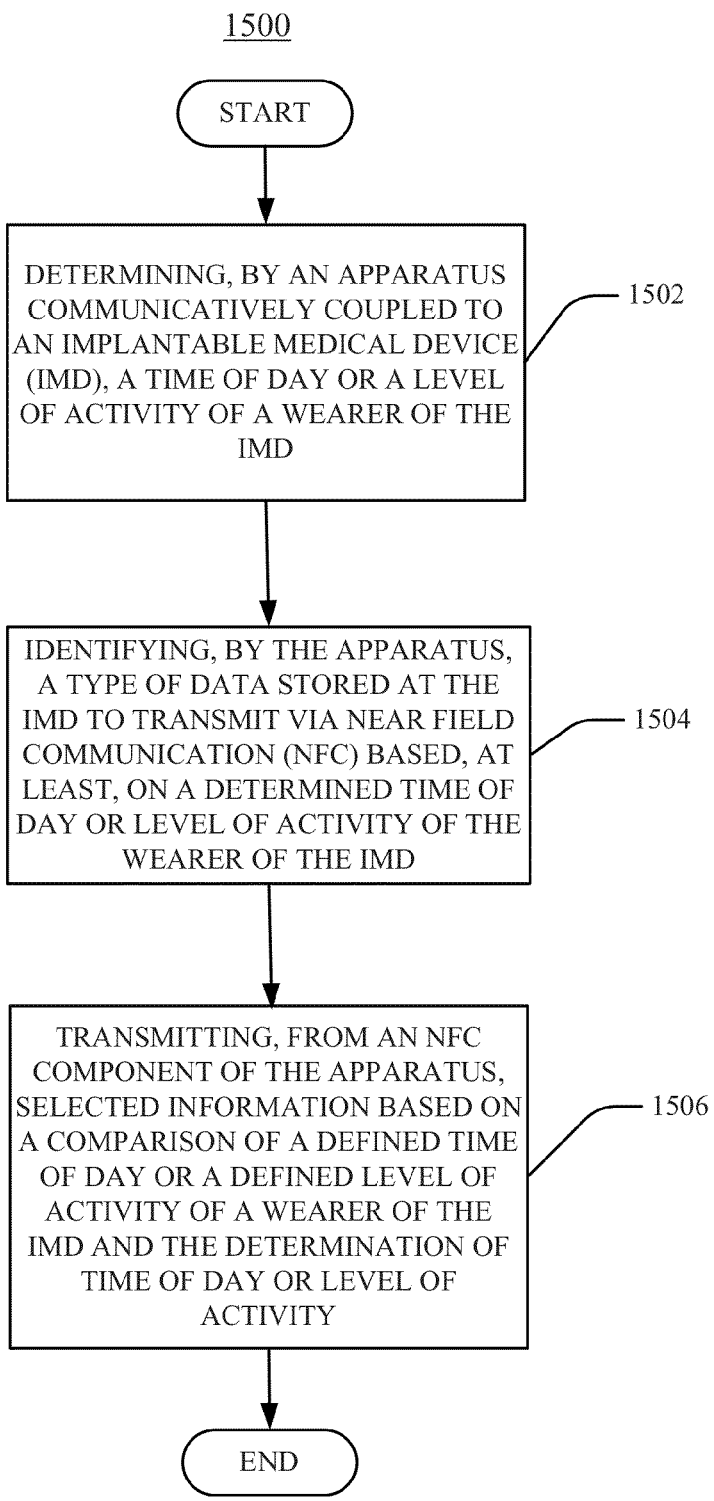

Turning now to FIG. 15, at 1502, method 1500 includes determining, by an apparatus communicatively coupled to an IMD, a time of day or level of activity of a wearer of the IMD. At 1504, method 1500 includes identifying, by the apparatus, a type of data stored at the IMD to transmit via NFC based, at least, on a determined time of day or level of activity of the wearer of the IMD.

At 1506, method 1500 includes transmitting, from an NFC component of the apparatus, selected information based on a comparison of a defined time of day or a defined level of activity and the determination of the actual time of day or level of activity. In some embodiments, for example, if a determination is made that a wearer of an IMD is asleep, an extensive data dump can be facilitated via NFC to a nearby NFC device (e.g., smart phone or wand on a nightstand of the wearer of the IMD).

These embodiments can be advantageous because with particular IMDs (e.g., pacemakers), monitoring is performed at designated times (as compared to being performed continuously or continually). Typically, transmission of relatively large amounts of data is performed at this time from the IMD. As such, a surge of power is often needed when performing the data transfer. Accordingly, in various embodiments, data transfer can be performed while the wearer of the IMD is asleep or during times of low activity and using NFC communication. For example, an NFC wand can be worn in a stethoscope fashion while asleep to facilitate data transfer. As another example, a wearable device can be worn. As another example, a smart phone or wand can be provided nearby (e.g., nightstand) in cases in which communication can be provided over longer distances.

Figure 16:
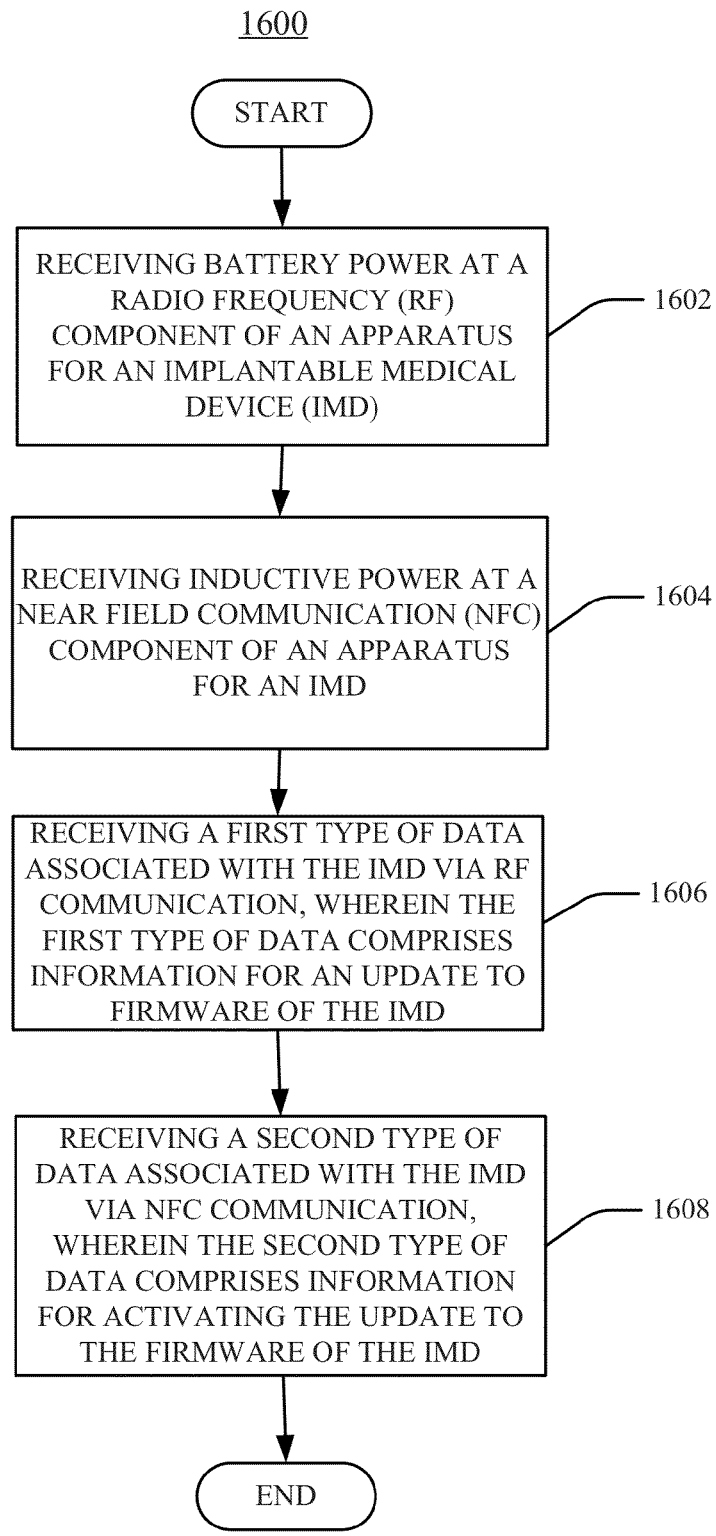

Turning now to FIG. 16, at 1602, method 1600 includes receiving, power at an RF component of an apparatus for an IMD. At 1604, method 1600 includes receiving inductive power at an NFC component of the apparatus. At 1606, method 1600 includes receiving a first type of data associated with the IMD via RF communication, wherein the first type of data comprises information for an update to firmware of the IMD. At 1608, method 1600 includes receiving a second type of data associate with the IMD via NFC communication, wherein the second type of data comprises information for activating the update to the firmware of the IMD. In various embodiments, the information is for an update to (or activating an update to) any software or application of the IMD.

Accordingly, this embodiment can advantageously limit activation of updates to the IMD to NFC-enabled devices. As such, because NFC communication requires very close proximity to the wearer of the IMD, and the wearer of the IMD is more likely to trust the NFC-enabled external device and/or personnel handling such device, greater safety is accomplished by reducing the likelihood of unintended or unwanted updates to the IMD.

Turning now to FIG. 13, at 1302, method 1300 includes determining, by an IMD system including a processor and having an RF component and an NFC component, whether an amount of battery power is sufficient for powering the RF component.

Some of the embodiments described herein can be practiced in computing environments and/or in collaboration with computing environments. In these environments, certain tasks can be performed by remote processing devices that are linked through a communications network. Also, some of the embodiments include computing devices having computer-executable instructions that can be executed by processors to perform one or more different functions. Those skilled in the art will recognize that the embodiments can be also implemented in combination with hardware and/or software.

Figure 17:
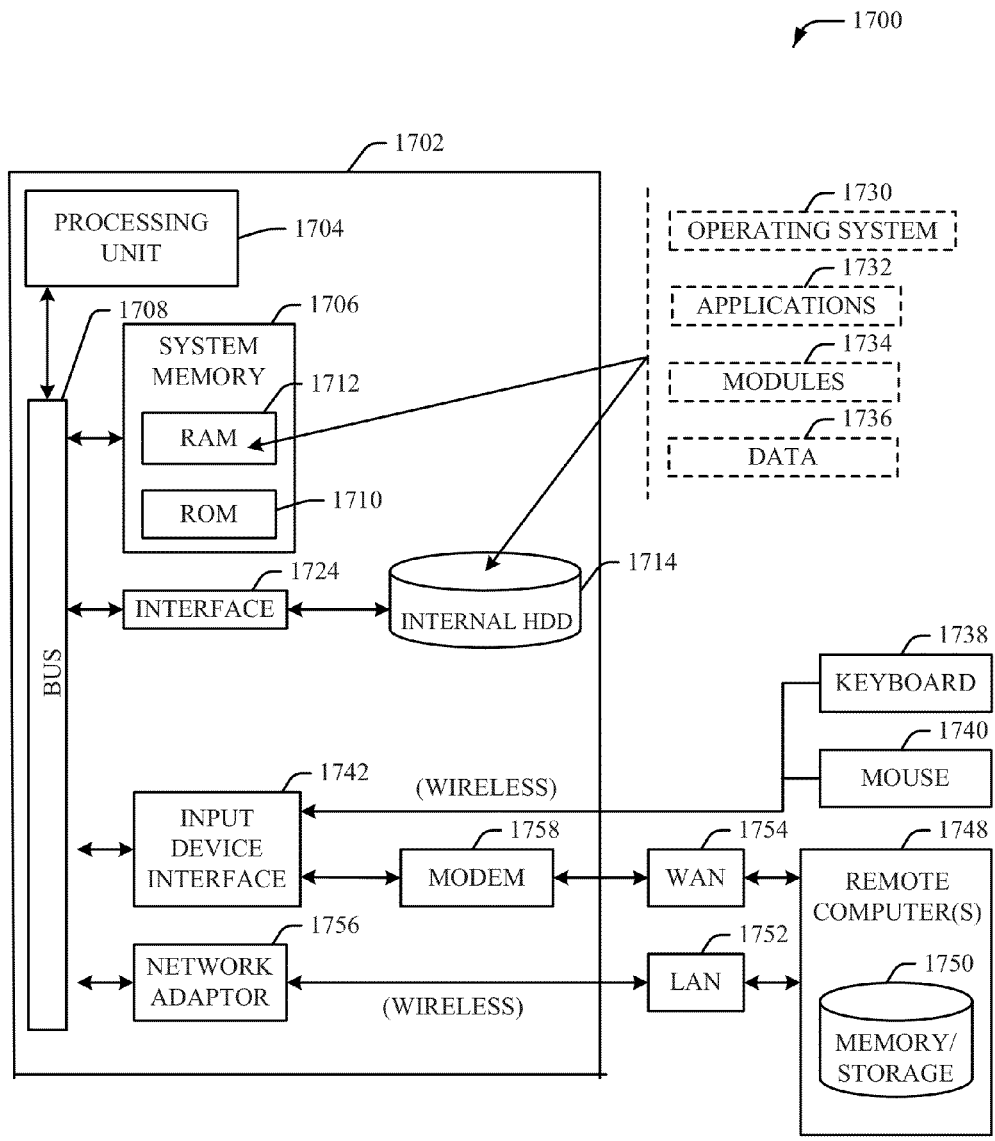
FIG. 17 illustrates a block diagram of a computer operable to facilitate processing for facilitating longevity extension of IMDs in accordance with embodiments described herein.

FIG. 17 illustrates a block diagram of a computer operable to facilitate processing for IMD extension of longevity in accordance with embodiments described herein. The computer can be provided in any one of the IMD assemblies, IMDs or other components thereof. In order to provide additional context for various embodiments described herein, FIG. 17 and the following discussion are intended to provide a brief, general description of a suitable computing environment 1900 in which the various embodiments of the embodiment described herein can be implemented.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

Computing devices typically include a variety of media, which can include computer-readable storage media and/or communications media, which two terms are used herein differently from one another as follows. Computer-readable storage media can be any available storage media that can be accessed by the computer and includes both volatile and nonvolatile media, removable and non-removable media. By way of example, and not limitation, computer-readable storage media can be implemented in connection with any method or technology for storage of information such as computer-readable instructions, program modules, structured data or unstructured data. Tangible and/or non-transitory computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD) or other optical disk storage, magnetic cassettes, magnetic tape, magnetic disk storage, other magnetic storage devices and/or other media that can be used to store desired information. Computer-readable storage media can be accessed by one or more local or remote computing devices, e.g., via access requests, queries or other data retrieval protocols, for a variety of operations with respect to the information stored by the medium.

In this regard, the term "tangible" herein as applied to storage, memory or computer-readable media, is to be understood to exclude only propagating intangible signals per se as a modifier and does not relinquish coverage of all standard storage, memory or computer-readable media that are not only propagating intangible signals per se.

In this regard, the term "non-transitory" herein as applied to storage, memory or computer-readable media, is to be understood to exclude only propagating transitory signals per se as a modifier and does not relinquish coverage of all standard storage, memory or computer-readable media that are not only propagating transitory signals per se.

Communications media typically embody computer-readable instructions, data structures, program modules or other structured or unstructured data in a data signal such as a modulated data signal, e.g., a channel wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

With reference again to FIG. 17, the example environment 1700 for implementing various aspects of the embodiments described herein includes a computer 1702, the computer 1702 including a processing unit 1704, a system memory 1706 and a system bus 1708. The system bus 1708 couples system components including, but not limited to, the system memory 1706 to the processing unit 1704. The processing unit 1704 can be any of various commercially available processors. Dual microprocessors and other multi-processor architectures can also be employed as the processing unit 1704.

The system bus 1708 can be any of several types of bus structure that can further interconnect to a memory bus (with or without a memory controller), a peripheral bus, and a local bus using any of a variety of commercially available bus architectures. The system memory 1706 includes ROM 1710 and RAM 1712. A basic input/output system (BIOS) can be stored in a non-volatile memory such as ROM, erasable programmable read only memory (EPROM), EEPROM, which BIOS contains the basic routines that help to transfer information between elements within the computer 1702, such as during startup. The RAM 1712 can also include a high-speed RAM such as static RAM for caching data.

The computer 1702 further includes an internal hard disk drive (HDD) 1714 (e.g., Enhanced Integrated Drive Electronics (EIDE), Serial Advanced Technology Attachment (SATA)). The HDD 1714 can be connected to the system bus 1708 by a hard disk drive interface 1704. The drives and their associated computer-readable storage media provide nonvolatile storage of data, data structures, computer-executable instructions, and so forth. For the computer 1702, the drives and storage media accommodate the storage of any data in a suitable digital format.

A number of program modules can be stored in the drives and RAM 1712, including an operating system 1730, one or more application programs 1732, other program modules 1734 and program data 1736. All or portions of the operating system, applications, modules, and/or data can also be cached in the RAM 1712. The systems and methods described herein can be implemented utilizing various commercially available operating systems or combinations of operating systems.

A mobile device can enter commands and information into the computer 1702 through one or more wireless input devices, e.g., a wireless keyboard 1738 and a pointing device, such as a wireless mouse 1740. Other input devices (not shown) can include a smart phone, tablet, laptop, wand, wearable device or the like. These and other input devices are often connected to the processing unit 1704 through an input device interface 1742 that can be coupled to the system bus 1708, but can be connected by other interfaces, such as a parallel port, an IEEE 1394 serial port, a game port and/or a universal serial bus (USB) port.

The computer 1702 can operate in a networked environment using logical connections via wired and/or wireless communications to one or more remote computers, such as a remote computer(s) 1748. The remote computer(s) 1748 can be a workstation, a server computer, a router, a personal computer, portable computer, microprocessor-based entertainment appliance, a peer device or other common network node, and typically includes many or all of the elements described relative to the computer 1702, although, for purposes of brevity, only a memory/storage device 1750 is illustrated. The logical connections depicted include wired/wireless connectivity to a local area network (LAN) 1752 and/or larger networks, e.g., a wide area network (WAN) 1754. Such LAN and WAN networking environments are commonplace in offices (e.g., medical facility offices, hospital offices) and companies, and facilitate enterprise-wide computer networks, such as intranets, all of which can connect to a global communications network (e.g., the Internet).

When used in a LAN networking environment, the computer 1702 can be connected to the local network 1752 through a wired and/or wireless communication network interface or adapter 1756. The adapter 1756 can facilitate wired or wireless communication to the LAN 1752, which can also include a wireless AP disposed thereon for communicating with the wireless adapter 1756.

When used in a WAN networking environment, the computer 1702 can include a modem 1758 or can be connected to a communications server on the WAN 1754 or has other means for establishing communications over the WAN 1754, such as by way of the Internet. The modem 1758, which can be internal or external and a wired or wireless device, can be connected to the system bus 1708 via the input device interface 1742. In a networked environment, program modules depicted relative to the computer 1702 or portions thereof, can be stored in the remote memory/storage device 1750. It will be appreciated that the network connections shown are example and other means of establishing a communications link between the computers can be used.

The computer 1702 can be operable to communicate with any wireless devices or entities operatively disposed in wireless communication. This can include NFC, Wireless Fidelity (Wi-Fi) and BLE wireless technologies. Thus, the communication can be a defined structure as with a conventional network or simply an ad hoc communication between at least two devices.

NFC can allow point-to-point connection to an NFC-enabled device in the NFC field of an IMD within the home or at any location. NFC technology can be facilitated using an NFC-enabled smart phone, tablet or other device that can be brought within 3-4 cms of an implanted NFC component. NFC networks typically provide a maximum data rate of 424 Kbps, although data rates can range from 106 Kbps to 424 Kbps. NFC networks typically operate at a carrier frequency of 13.56 MHz. NFC technology communication is typically over a range not exceeding 0.1 m and setup time is less than 0.1 second (s). Low power (e.g., 15 mA) reading of data can be performed by an NFC device.

Wi-Fi can allow connection to the Internet from a couch at home, a bed in a hotel room or a conference room at work, without wires. Wi-Fi is a wireless technology similar to that used in a cell phone that enables such devices, e.g., computers, to send and receive data indoors and out. Wi-Fi networks use radio technologies called IEEE 802.11 (a, b, g, n, etc.) to provide secure, reliable, fast wireless connectivity. A Wi-Fi network can be used to connect computers to each other, to the Internet, and to wired networks (which can use IEEE 802.3 or Ethernet). Wi-Fi networks operate in the unlicensed 2.4 and 5 GHz radio bands, at an 11 Mbps (802.11a) or 54 Mbps (802.11b) data rate, for example or with products that contain both bands (dual band), so the networks can provide real-world performance similar to the basic 10BaseT wired Ethernet networks used in many offices.

The embodiments (e.g., embodiments of switching components 126, 408) described herein can employ AI to facilitate automating one or more features described herein. The embodiments (e.g., in connection with automatically identifying acquired cell sites that provide a maximum value/benefit after addition to an existing communication network) can employ various AI-based schemes for carrying out various embodiments thereof. Moreover, the classifier can be employed to determine a ranking or priority of each cell site of an acquired network. A classifier is a function that maps an input attribute vector, $x=(x1, x2, x3, x4, \ldots, xn)$, to a confidence that the input belongs to a class, that is, $f(x)=confidence(class)$. Such classification can employ a probabilistic and/or statistical-based analysis (e.g., factoring into the analysis utilities and costs) to prognose or infer an action that a mobile device desires to be automatically performed. A support vector machine (SVM) is an example of a classifier that can be employed. The SVM operates by finding a hypersurface in the space of possible inputs, which the hypersurface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

As will be readily appreciated, one or more of the embodiments can employ classifiers that are explicitly trained (e.g., via a generic training data) as well as implicitly trained (e.g., via observing mobile device behavior, operator preferences, historical information, receiving extrinsic information). For example, SVMs can be configured via a learning or training phase within a classifier constructor and feature selection module. Thus, the classifier(s) can be used to automatically learn and perform a number of functions, including but not limited to determining according to a predetermined criteria which of the acquired cell sites will benefit a maximum number of subscribers and/or which of the acquired cell sites will add minimum value to the existing communication network coverage, etc.

As employed herein, the term "processor" can refer to substantially any computing processing unit or device comprising, but not limited to comprising, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components or any combination thereof designed to perform the functions described herein. Processors can exploit nano-scale architectures such as, but not limited to, molecular and quantum-dot based transistors, switches and gates, in order to optimize space usage or enhance performance of mobile device equipment. A processor can also be implemented as a combination of computing processing units.

Memory disclosed herein can include volatile memory or nonvolatile memory or can include both volatile and nonvolatile memory. By way of illustration, and not limitation, nonvolatile memory can include ROM, programmable ROM (PROM), electrically programmable ROM (EPROM), electrically erasable PROM (EEPROM) or flash memory. Volatile memory can include RAM, which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The memory (e.g., data storages, databases) of the embodiments are intended to comprise, without being limited to, these and any other suitable types of memory.

As used herein, terms such as "data storage," "database," and substantially any other information storage component relevant to operation and functionality of a component, refer to "memory components," or entities embodied in a "memory" or components comprising the memory. It will be appreciated that the memory components or computer-readable storage media, described herein can be either volatile memory or nonvolatile memory or can include both volatile and nonvolatile memory.

What has been described above includes mere examples of various embodiments. It is, of course, not possible to describe every conceivable combination of components or methodologies for purposes of describing these examples, but one of ordinary skill in the art can recognize that many further combinations and permutations of the present embodiments are possible. Accordingly, the embodiments disclosed and/or claimed herein are intended to embrace all such alterations, modifications and variations that fall within the spirit and scope of the detailed description and the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. An implantable medical device (IMD) comprising:
a battery;
a first communication component configured to provide a first communication type, and configured to be powered by the battery;
a second communication component configured to provide a second communication type, wherein the second communication component is powered by induction, and configured to provide unidirectional access to information stored at the IMD, by a device external to the IMD, based on detection of inductive power at a coil of the second communication component; and is powered by the battery, and configured to engage in bi-directional communication with the device external to the IMD, based on a lack of detection of the inductive power at the coil of the second communication component; and
a processor configured to select at least one of the first communication component or the second communication component to perform communication based, at least, on a defined condition being satisfied.

2. The IMD of claim 1, wherein the defined condition comprises availability of required power from the battery for the first communication type.

3. The IMD of claim 2, wherein the processor is configured to select the first communication component based, at least, on the availability of required power from the battery for the first communication type.

4. The IMD of claim 2, wherein the processor is configured to select the second communication component based, at least, on non-availability of required power from the battery for the first communication type.

5. The IMD of claim 1, wherein the first communication component comprises a component requiring a first amount of power from the battery, and wherein the second communication component comprises a component requiring a second amount of power from the battery, wherein the first amount of power is greater than the second amount of power.

6. The IMD of claim 1, wherein the first communication component comprises a component configured to perform radio frequency communication.

7. The IMD of claim 6, wherein the second communication component comprises a component configured to perform near field communication.

8. The IMD of claim 1, wherein the detection of the inductive power and a provisioning of the unidirectional access to information occur during a first time period.

9. The IMD of claim 8, wherein the bi-directional communication occurs during a second time period, and wherein the first time period and the second time period are substantially non-overlapping.

10. The IMD of claim 1, wherein the battery is configured to be re-charged from the inductive power detected at the second communication component.

11. The IMD of claim 1, wherein the first communication component is further configured to communicate a first type of data via the first communication type, and the second communication component is further configured to communicate a second type of data via the second communication type, and wherein the second type of data has a greater level of sensitivity than the first type of data.

* * * * *